(12) United States Patent
French et al.

(10) Patent No.: US 6,317,207 B2
(45) Date of Patent: Nov. 13, 2001

(54) FREQUENCY-DOMAIN LIGHT DETECTION DEVICE

(75) Inventors: Todd E. French, Cupertino; David P. Stumbo, Belmont; Douglas N. Modlin, Palo Alto, all of CA (US)

(73) Assignee: LJL Biosystems, Inc., Sunnyvale, CA (US)

( * ) Notice: Subject to any disclaimer, the term of this patent is extended or adjusted under 35 U.S.C. 154(b) by 0 days.

(21) Appl. No.: 09/767,579

(22) Filed: Jan. 22, 2001

Related U.S. Application Data

(63) Continuation of application No. PCT/US00/04543, filed on Feb. 22, 2000.
(60) Provisional application No. 60/121,229, filed on Feb. 23, 1999.

(51) Int. Cl.[7] .................................................. G01N 21/64
(52) U.S. Cl. .................... 356/317; 356/318; 356/417; 250/458.1; 250/459.1
(58) Field of Search ..................... 356/317, 418, 356/417, 447, 246, 303, 323, 326; 250/458.1, 459.1, 205; 600/317; 436/172

(56) References Cited

U.S. PATENT DOCUMENTS

| | | |
|---|---|---|
| 2,719,214 | 9/1955 | Potter . |
| 3,013,467 | 12/1961 | Minsky . |
| 3,423,581 | 1/1969 | Baer . |
| 3,516,736 | 6/1970 | Weaver . |
| 3,849,654 | 11/1974 | Malvin . |
| 3,885,162 | 5/1975 | Geertz . |
| 3,932,023 | 1/1976 | Humer . |
| 4,011,451 | 3/1977 | Nelson . |
| 4,067,653 | 1/1978 | Fletcher et al. . |
| 4,074,939 | 2/1978 | Rabl . |

(List continued on next page.)

FOREIGN PATENT DOCUMENTS

| | | |
|---|---|---|
| 0 222 341 A1 | 5/1987 | (EP) . |
| 0 266 881 A2 | 11/1988 | (EP) . |
| 0 977 037 A1 | 7/1999 | (EP) . |
| 0 993 916 A2 | 10/1999 | (EP) . |
| 0 995 555 A1 | 10/1999 | (EP) . |

(List continued on next page.)

OTHER PUBLICATIONS

*Standard Handbook for Electrical Engineers,* Donald G. Fink and H. Wayne Beaty, pp. 22–2 through 22–5, 11th ed., 1978.
*Fundamentals of Light Microscopy,* Spencer, Cambridge University Press, 1982.
Joseph R. Lakowicz, *Principles of Fluorescence Spectroscopy,* First Edition, Sep. 1983.
Basic Fluorescence Microscopy, Taylor et al., *Methods in Cell Biology,* vol. 29, pp. 207–237, 1989.
Quantitative Fluorescence Miscroscopy Using Photomultiplier Tubes and Imaging Detectors, Wampler et al., *Methods in Cell Biology,* vol. 30, pp. 239–267, 1989.

(List continued on next page.)

*Primary Examiner*—Frank G. Font
*Assistant Examiner*—Layla Lauchman
(74) *Attorney, Agent, or Firm*—Kolisch, Hartwell, Dickinson, McCormack & Heuser

(57) ABSTRACT

Apparatus and methods for determining temporal properties of photoluminescent samples using frequency-domain photoluminescence measurements, where the measurements may include photon counting and/or the separation of measured luminescence into potentially overlapping time bins.

36 Claims, 16 Drawing Sheets

U.S. PATENT DOCUMENTS

| | | |
|---|---|---|
| 4,076,420 | 2/1978 | De Maeyer et al. . |
| 4,100,416 | 7/1978 | Hirschfeld . |
| 4,144,452 | 3/1979 | Harte . |
| 4,150,870 | 4/1979 | d'Auria . |
| 4,203,670 | 5/1980 | Bromberg . |
| 4,240,751 | 12/1980 | Linnecke et al. . |
| 4,296,326 | 10/1981 | Halsop et al. . |
| 4,397,560 | 8/1983 | Andreson . |
| 4,451,149 | 5/1984 | Noeller . |
| 4,451,433 | 5/1984 | Yamashita et al. . |
| 4,485,430 | 11/1984 | Fustel . |
| 4,501,970 | 2/1985 | Nelson . |
| 4,567,847 | 2/1986 | Linner . |
| 4,591,550 | 5/1986 | Hafeman et al. . |
| 4,626,684 | 12/1986 | Landa . |
| 4,646,214 | 2/1987 | Mendleski . |
| 4,685,801 | 8/1987 | Minekane . |
| 4,699,512 | 10/1987 | Koshi . |
| 4,704,255 | 11/1987 | Jolley . |
| 4,707,067 | 11/1987 | Haberland et al. . |
| 4,730,921 | 3/1988 | Klein et al. . |
| 4,737,464 | 4/1988 | McConnel et al. . |
| 4,738,825 | 4/1988 | Kelln et al. . |
| 4,741,619 | 5/1988 | Humphries et al. . |
| 4,753,501 | 6/1988 | Battle . |
| 4,758,786 | 7/1988 | Hafeman . |
| 4,762,420 | 8/1988 | Bowley . |
| 4,772,453 | 9/1988 | Lisenbee . |
| 4,784,275 | 11/1988 | Fridge . |
| 4,802,768 | 2/1989 | Gifford et al. . |
| 4,808,828 | 2/1989 | Kitamori et al. . |
| 4,810,096 | 3/1989 | Russel et al. . |
| 4,826,660 | 5/1989 | Smith et al. . |
| 4,855,930 | 8/1989 | Chao et al. . |
| 4,868,103 | 9/1989 | Stavrianopoulos et al. . |
| 4,873,633 | 10/1989 | Mezei et al. . |
| 4,877,965 | 10/1989 | Dandliker et al. . |
| 4,885,087 | 12/1989 | Kopf . |
| 4,892,409 | 1/1990 | Smith . |
| 4,897,548 | 1/1990 | Döme et al. . |
| 4,923,819 | 5/1990 | Fernandez et al. . |
| 4,931,402 | 6/1990 | Abplanalp . |
| 4,936,682 | 6/1990 | Hoyt . |
| 4,948,442 | 8/1990 | Manns . |
| 4,963,815 | 10/1990 | Hafeman . |
| 4,968,148 | 11/1990 | Chow et al. . |
| 4,979,821 | 12/1990 | Schutt et al. . |
| 5,009,488 | 4/1991 | Fay et al. . |
| 5,018,866 | 5/1991 | Osten . |
| 5,020,995 | 6/1991 | Levy . |
| 5,034,613 | 7/1991 | Denk et al. . |
| 5,039,219 | 8/1991 | James et al. . |
| 5,047,215 | 9/1991 | Manns . |
| 5,058,045 | 10/1991 | Ma . |
| 5,082,628 | 1/1992 | Andreotti et al. . |
| 5,084,246 | 1/1992 | Lyman et al. . |
| 5,091,652 | 2/1992 | Mathies et al. . |
| 5,095,517 | 3/1992 | Monguzzi et al. . |
| 5,096,807 | 3/1992 | Leaback . |
| 5,164,319 | 11/1992 | Hafeman et al. . |
| 5,169,601 | 12/1992 | Ohta et al. . |
| 5,192,510 | 3/1993 | Zoha et al. . |
| 5,196,709 | 3/1993 | Berndt et al. . |
| 5,198,670 | 3/1993 | VanCauter et al. . |
| 5,206,568 | 4/1993 | Björnson et al. . |
| 5,208,161 | 5/1993 | Saunders et al. . |
| 5,208,651 | 5/1993 | Buican . |
| 5,216,488 | 6/1993 | Tuunanen et al. . |
| 5,225,164 | 7/1993 | Astle . |
| 5,257,202 | 10/1993 | Feddersen et al. . |
| 5,270,788 | 12/1993 | Cercek et al. . |
| 5,273,718 | 12/1993 | Sköld et al. . |
| 5,275,951 | 1/1994 | Chow et al. . |
| 5,281,825 | 1/1994 | Berndt et al. . |
| 5,289,407 | 2/1994 | Strickler et al. . |
| 5,307,144 | 4/1994 | Hiroshi et al. . |
| 5,315,015 | 5/1994 | Hui et al. . |
| 5,317,485 | 5/1994 | Merjanian . |
| 5,319,436 | 6/1994 | Manns et al. . |
| 5,323,008 | 6/1994 | Studholme et al. . |
| 5,323,010 | 6/1994 | Gratton et al. . |
| 5,340,716 | 8/1994 | Ullman et al. . |
| 5,340,747 | 8/1994 | Eden . |
| 5,341,215 | 8/1994 | Seher . |
| 5,353,112 | 10/1994 | Smith . |
| 5,355,215 | 10/1994 | Schroeder et al. . |
| 5,357,095 | 10/1994 | Weyrauch et al. . |
| 5,361,626 | 11/1994 | Colligan et al. . |
| 5,384,093 | 1/1995 | Ootani et al. . |
| 5,401,465 | 3/1995 | Smethers et al. . |
| 5,418,371 | 5/1995 | Aslund et al. . |
| 5,420,408 | 5/1995 | Weyrauch et al. . |
| 5,436,718 | 7/1995 | Fernandes et al. . |
| 5,445,935 | 8/1995 | Royer . |
| 5,449,921 | 9/1995 | Baba . |
| 5,457,527 | 10/1995 | Manns et al. . |
| 5,459,300 | 10/1995 | Kasman . |
| 5,480,804 | 1/1996 | Niwa et al. . |
| 5,485,530 | 1/1996 | Lakowicz et al. . |
| 5,487,872 | 1/1996 | Hafeman et al. . |
| 5,491,343 | 2/1996 | Brooker . |
| 5,500,188 | 3/1996 | Hafeman et al. . |
| 5,504,337 | 4/1996 | Lakowicz et al. . |
| 5,512,492 | 4/1996 | Herron et al. . |
| 5,523,573 | 6/1996 | Hänninen et al. . |
| 5,527,684 | 6/1996 | Mabile et al. . |
| 5,528,046 | 6/1996 | Ishikawa . |
| 5,537,343 | 7/1996 | Kikinis et al. . |
| 5,541,113 | 7/1996 | Siddigi et al. . |
| 5,542,012 | 7/1996 | Fernandez . |
| 5,557,398 | 9/1996 | Wechsler et al. . |
| 5,561,068 | 10/1996 | Rounbehler et al. . |
| 5,589,136 | 12/1996 | Northrup et al. . |
| 5,589,350 | 12/1996 | Bochner . |
| 5,589,351 | 12/1996 | Harootunian . |
| 5,592,289 | 1/1997 | Norris . |
| 5,593,867 | 1/1997 | Walker et al. . |
| 5,595,710 | 1/1997 | Van Dusen et al. . |
| 5,599,500 | 2/1997 | Jones . |
| 5,604,130 | 2/1997 | Warner et al. . |
| 5,620,894 | 4/1997 | Barger et al. . |
| 5,626,134 | 5/1997 | Zuckerman . |
| 5,631,734 | 5/1997 | Stern et al. . |
| 5,633,724 | 5/1997 | King et al. . |
| 5,635,402 | 6/1997 | Alfano et al. . |
| 5,641,633 | 6/1997 | Linn et al. . |
| 5,645,800 | 7/1997 | Masterson et al. . |
| 5,663,545 | 9/1997 | Marquiss . |
| 5,670,113 | 9/1997 | Akong et al. . |
| 5,672,880 | 9/1997 | Kain . |
| 5,676,943 | 10/1997 | Baetge et al. . |
| 5,677,196 | 10/1997 | Herron et al. . |
| 5,679,310 | 10/1997 | Manns . |
| 5,736,410 | 4/1998 | Zarling et al. . |
| 5,738,825 | 4/1998 | Rudigier et al. . |
| 5,741,554 | 4/1998 | Tisone . |
| 5,746,974 | 5/1998 | Massey et al. . |
| 5,750,410 | 5/1998 | Dou et al. . |
| 5,756,292 | 5/1998 | Royer . |
| 5,766,875 | 6/1998 | Hafeman et al. . |
| 5,780,857 | 7/1998 | Harju et al. . |

| | | |
|---|---|---|
| 5,798,083 | 8/1998 | Massey et al. |
| 5,798,085 | 8/1998 | Seaton et al. |
| 5,825,617 | 10/1998 | Kochis et al. |
| 5,842,582 | 12/1998 | DeStefano, Jr. |
| 5,888,454 | 3/1999 | Leistner et al. |
| 5,905,571 | 5/1999 | Butler et al. |
| 5,933,232 | 8/1999 | Atzler et al. |
| 5,959,738 | 9/1999 | Hafeman et al. |
| 5,989,835 | 11/1999 | Dunlay et al. |
| 5,993,746 | 11/1999 | Priha et al. |
| 6,020,591 | 2/2000 | Harter et al. |
| 6,025,985 | 2/2000 | Leytes et al. |
| 6,033,100 | 3/2000 | Marquiss et al. |
| 6,071,748 | 6/2000 | Modlin et al. |
| 6,097,025 | 8/2000 | Modlin et al. |
| 6,137,584 | 10/2000 | Seidel et al. |
| 6,159,425 | 12/2000 | Edwards et al. |
| 6,187,267 | 2/2001 | Taylor et al. |

FOREIGN PATENT DOCUMENTS

| | | |
|---|---|---|
| 1 003 020 A1 | 5/2000 | (EP) . |
| 1 003 039 A1 | 5/2000 | (EP) . |
| 2228081 | 8/1990 | (GB) . |
| 2215838 | 9/1990 | (GB) . |
| WO99/04288 | 1/1999 | (WO) . |
| WO99/08233 | 2/1999 | (WO) . |
| WO99/23466 | 5/1999 | (WO) . |
| WO99/37203 | 7/1999 | (WO) . |
| WO99/42817 | 8/1999 | (WO) . |
| WO99/54711 | 10/1999 | (WO) . |
| WO00/04364 | 1/2000 | (WO) . |
| WO00/06989 | 2/2000 | (WO) . |
| WO00/06990 | 2/2000 | (WO) . |
| WO00/06991 | 2/2000 | (WO) . |
| WO00/42209 | 7/2000 | (WO) . |
| WO00/50877 | 8/2000 | (WO) . |
| WO00/55372 | 9/2000 | (WO) . |
| WO00/66269 | 11/2000 | (WO) . |
| WO01/04608 | 1/2001 | (WO) . |

OTHER PUBLICATIONS

Three–Dimensional Confocal Fluorescence Microscopy, Brakenhoff et al., *Methods in Cell Biology*, vol. 30, pp. 379–389, 1989.
Laser Scanning Confocal Microscopy of Living Cells, Lemasters et al., *Optical Microscopy: Emerging Methods and Applications*, pp. 339–345, 1993.
Time–Resolved Fluorescence Lifetime Imaging, vandeVen et al., *Optical Microscopy: Emerging Methods and Applications*, pp. 373–389, 1993.
Electrochemiluminescence: A New Diagnostic and Research Tool, Yang et al., *Bio/Technology*, vol. 12, pp. 193–194, Feb. 1994.
Sorting Single Molecules: Application to Diagnostics and Evolutionary Biotechnology, Eigen et al., *PNAS*, vol. 91, pp. 5740–5747, 1994.
High Throughput Screening Using Dynamic Fluorescence, Swift et al., *SPIE*, vol. 2388, pp. 182–189, Feb. 6–8, 1995.
Genesis Series Robotic Sample Processors brochure, Tecan AG, Oct. 1997.
Genesis Robotic Microprocessor brochure, Tecan AG, Nov. 1997.
A Measure of Brilliance, TR717 Microplate Luminometer brochure, Tropix, Inc., 1997.
Advanced Microplate Detection Systems brochure, Tecan AG, Feb. 1998.
The SPECTRA Family brochure, Tecan AG, Feb. 1998.
Assist Plate Handling Device brochure, Labsystems, May 1998.
Wallac Time–Resolved Fluorometry—The Key to Improved Assay Sensitivity, internet description pages, Jul. 7, 1998.
Wallac 1234 DELFIA Fluorometer, internet decription page, Jul. 7, 1998.
Wallac 1420 VICTOR Multilabel Counter, internet decription pages, Jul. 7, 1998.
Wallac 1420 VICTOR$^2$ Multilabel Counter, internet description pages, Jul. 7, 1998.
Wallac 1442 ARTHUR Multi–wavelength Fluoroimager, internet decription page, Jul. 7, 1998.
Wallac Labeling Reagents for Time–resolved Fluorometry, internet decription pages, Jul. 7, 1998.
Genesis Assay Workstation brochure, Tecan AG, Jul. 1998.
Genesis Logistics Workstation borchure, Tecan AG, Jul. 1998.
Polarion brochure, Tecan AG, Aug. 1998.
CytoFluor Fluorescence Multi–Well Plate Reader brochure, PerSeptive Biosystems, 1998.
Microplate Instrumentation Catalogue 1998, Labsystems, 1998.
Fixed Polarizer Ellipsometry for Simple and Sensitive Detection of Thin Films Generated by Specific Molecular Interactions: Applications in Immunoassays and DNA Sequence Detection, Ostroff et al., *Clinical Chemistry*, 44:9, pp. 2031–2035, 1998.
Magellan, Instrument Control and Data Analysis Software brochure, Tecan AG, Nov. 1999.
TWISTER™, Tecan's Automated Microplate Handler brochure, Tecan AG, Nov. 1999.
A Microfabricated Fluorescence–Activated Cell Sorter, Fu et al. *Nature Biotechnology*, vol. 17, pp. 1109–1111, Nov. 1999.
Absorbance Readers brochure, Tecan AG, Dec. 1999.
ULTRA—The Solution for HTS and Assay Development brochure, Tecan Austria GMBH, Dec. 1999.
Principles of Flurorescence Spectroscopy, Joseph R. Lakowicz, Second Edition, 1999.
CyBi™—Lumax 1,536 brochure, CyBio AG, May 2000.
CyBi™—PlateSafe brochure, CyBio AG, May 2000.
SPECTRAmax® GEMINI XS brochure, Molecular Devices Corp., Jun. 2000.
SPECTRAmax® PLUS$^{384}$ brochure, Molecular Devices Corp., Jun. 2000.
Packard BioScience Company Introduces the Fusion™ Universal Microplate Analyzer press release, Packard BioScience Company, Jun. 29, 2000.
Labcyte: Research and Clinical Instruments for Life Sciences brochure, Arlena research LLC, Aug. 1, 2000.
Fusion™ Universal Microplate Analyzer, Packard BioScience Company, Aug. 2000.
CyBi™—Screen—Machine: One System—Many Solutions brochure, CyBio AG, 2000.
Acumen Explorer brochure, Acumen, undated.
FLIPR 384: Essential Technology for Drug Discovery brochure, Molecular Devices Corp., undated.
FLUOstar Galaxy brochure, BMG Labtechnologies GmbH, undated.
NEPHELOstar brochure, BMG Labtechnologies GmbH, undated.
LUMIstar Galaxy brochure, BMG Labtechnologies GmbH, undated.
POLARstar Galaxy brochure, BMG Labtechnologies GmbH, undated.
POLARstar Galaxy flyer, BMG Labtechnologies GmbH, undated.

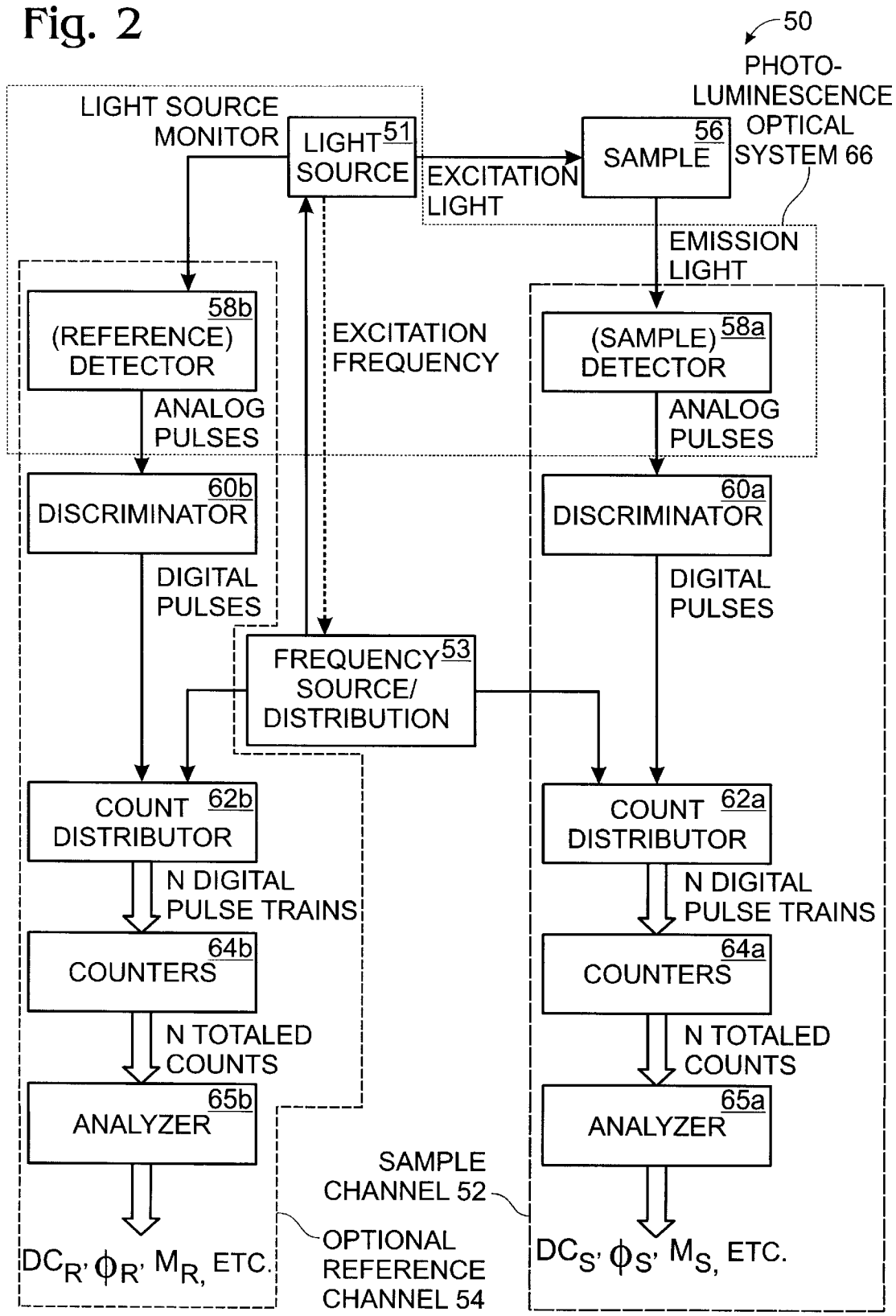

FREQUENCY-DOMAIN LIGHT DETECTION DEVICE

CROSS-REFERENCES

This application is a continuation of PCT Patent Application Ser. No. PCT/US00/04543, filed Feb. 22, 2000, which is incorporated herein by reference.

This application claims priority from the following U.S. provisional patent application, which is hereby incorporated by reference: Ser. No. 60/121,229, filed Feb. 23, 1999.

This application incorporates by reference the following U.S. patent applications: Ser. No. 09/062,472, filed Apr. 17, 1998; Ser. No. 09/160,533, filed Sep. 24, 1998; Ser. No. 09/349,733, filed Jul. 8, 1999; Ser. No. 09/468,440, filed Dec. 21, 1999; Ser. No. 09/478,819, filed Jan. 5, 2000; and Ser. No. 09/494,407, filed Jan. 28, 2000.

This application also incorporates by reference the following PCT patent applications: Ser. No. PCT/US98/23095, filed Oct. 30, 1998; Ser. No. PCT/US99/01656, filed Jan. 25, 1999; Ser. No. PCT/US99/03678, filed Feb. 19, 1999; Ser. No. PCT/US99/08410, filed Apr. 16, 1999; Ser. No. PCT/US99/16057, filed Jul. 15, 1999; Ser. No. PCT/US99/16453, filed Jul. 21, 1999; Ser. No. PCT/US99/16621, filed Jul. 23, 1999; Ser. No. PCT/US99/16286, filed Jul. 26, 1999; Ser. No. PCT/US99/16287, filed Jul. 26, 1999; Ser. No. PCT/US99/24707, filed Oct. 19, 1999; Ser. No. PCT/US00/00895, filed Jan. 14, 2000; and Ser. No. PCT/US00/03589, filed Feb. 11, 2000.

This application also incorporates by reference the following U.S. provisional patent applications: Ser. No. 60/124,686, filed Mar. 16, 1999; Ser. No. 60/125,346, filed Mar. 19, 1999; Ser. No. 60/130,149, filed Apr. 20, 1999; Ser. No. 60/132,262, filed May 3, 1999; Ser. No. 60/132,263, filed May 3, 1999; Ser. No. 60/135,284, filed May 21, 1999; Ser. No. 60/138,311, filed Jun. 9, 1999; Ser. No. 60/138,438, filed Jun. 10, 1999; Ser. No. 60/138,737, filed Jun. 11, 1999; Ser. No. 60/138,893, filed Jun. 11, 1999; Ser. No. 60/142,721, filed Jul. 7, 1999; Ser. No. 60/153,251, filed Sep. 10, 1999; Ser. No. 60/164,633, filed Nov. 10, 1999; Ser. No. 60/167,301, filed Nov. 24, 1999; Ser. No. 60/167,463, filed Nov. 24, 1999; Ser. No. 60/178,026, filed Jan. 26, 2000; Ser. No. 60/182,036, filed Feb. 11, 2000; and Ser. No. 60/182,419, filed Feb. 14, 2000.

This application also incorporates by reference the following publications: Richard P. Haugland, *Handbook of Fluorescent Probes and Research Chemicals* (6th ed. 1996); and Joseph R. Lakowicz, *Principles of Fluorescence Spectroscopy* (2nd ed. 1999).

FIELD OF THE INVENTION

The invention relates to photoluminescence. More particularly, the invention relates to apparatus and methods for determining temporal properties of photoluminescent samples using frequency-domain photoluminescence measurements based on photon counting and/or the separation of measured luminescence into potentially overlapping time bins.

BACKGROUND OF THE INVENTION

Luminescence is the emission of light from excited electronic states of luminescent atoms or molecules (i.e., "luminophores"). Luminescence generally refers to all emission of light, except incandescence, and may include photoluminescence, chemiluminescence, and electrochemiluminescence, among others. In photoluminescence, which includes fluorescence and phosphorescence, the excited electronic state is created by the absorption of electromagnetic radiation. In particular, the excited electronic state is created by the absorption of radiation having an energy sufficient to excite an electron from a low-energy ground state into a higher-energy excited state. The energy associated with the excited state subsequently may be lost through one or more of several mechanisms, including production of a photon through fluorescence, phosphorescence, or other mechanisms. Here, the terms luminescence and photoluminescence are used interchangeably, except where noted, and a reference to luminescence or luminophore should be understood to imply a reference to photoluminescence and photoluminophore, respectively.

Luminescence may be characterized by a number of parameters, including luminescence lifetime. The luminescence lifetime is the average time that a luminophore spends in the excited state prior to returning to the ground state.

Luminescence may be used in assays to study the properties and environment of luminescent analytes. The analyte may be the focus of the assay, or the analyte may act as a reporter to provide information about another material or target substance that is the focus of the assay. Luminescence assays may be based on various aspects of the luminescence, including its intensity, polarization, and lifetime, among others. Luminescence assays also may be based on time-independent (steady-state) and/or time-dependent (time-resolved) properties of the luminescence.

Time-resolved luminescence assays may be used to study the temporal properties of a sample. These temporal properties generally include any properties describing the time evolution of the sample or components of the sample. These properties include the time-dependent luminescence emission and time-dependent luminescence polarization (or, equivalently, anisotropy), among others. These properties also include coefficients for describing such properties, such as the luminescence lifetime and the rotational (or more generally the reorientational) correlation time.

Time-resolved luminescence may be measured using "time-domain" or "frequency-domain" techniques, each of which involves monitoring the time course of luminescence emission.

In a time-domain measurement, the time course of luminescence is monitored directly. Typically, a sample containing a luminescent analyte is illuminated using a narrow pulse of light, and the time dependence of the intensity of the resulting luminescence emission is observed. For a simple luminophore, the luminescence commonly follows a single-exponential decay, so that the luminescence lifetime can (in principle) be determined from the time required for the intensity to fall to 1/e of its initial value.

In a frequency-domain measurement, the time course of luminescence is monitored indirectly, in frequency space. Typically, the sample is illuminated using intensity-modulated incident light, where the modulation may be characterized by a characteristic time, such as a period. Frequency-domain analysis may use almost any modulation profile. However, because virtually any modulation profile can be expressed as a sum of sinusoidal components using Fourier analysis, frequency-domain analysis may be understood by studying the relationship between excitation and emission for sinusoidal modulation.

FIG. 1 shows the relationship between excitation and emission in a frequency-domain experiment, where the excitation light is modulated sinusoidally at a single modulation frequency f. The resulting luminescence emission is modulated at the same frequency as the excitation light. However, the intensity of the emission will lag the intensity of the excitation by a phase angle (phase) φ and will be demodulated by a demodulation factor (modulation) M. Specifically, the phase φ is the phase difference between the excitation and emission, and the modulation M is the ratio of the AC amplitude to the DC offset for the emission, relative to the ratio of the AC amplitude to the DC offset for the excitation. The phase and modulation are related to the luminescence lifetime τ by the following equations:

$$\omega\tau = \tan(\phi) \qquad (1)$$

$$\omega\tau = \sqrt{\frac{1}{M^2} - 1} \qquad (2)$$

Here, ω is the angular modulation frequency, which equals 2π times the modulation frequency. Significantly, unlike in time-domain measurements, the measured quantities (phase and modulation) re directly related to the luminescence lifetime. For maximum sensitivity, the angular modulation frequency should be roughly the inverse of the luminescence lifetime. Typical luminescence lifetimes vary from less than about 1 nanosecond to greater than about 10 milliseconds. Therefore, instruments for measuring luminescence lifetimes should be able to cover modulation frequencies from less than about 20 Hz to greater than about 200 MHz.

A similar approach may be used to study other temporal properties of a luminescent sample, such as time-resolved luminescence polarization, which may be characterized by a rotational (or more generally a reorientational) correlation time. The use of standard frequency-domain techniques to study such properties is described in the above-identified patent applications and in Joseph R. Lakowicz, *Principles of Fluorescence Spectroscopy* (2$^{nd}$ ed. 1999), each of which is incorporated herein by reference.

Frequency-domain measurements typically are conducted at high frequencies, especially for short-lifetime luminophores. To simplify these measurements, the emission signal may be converted to a lower frequency, as follows. In radio-frequency (RF) signal detection, an input frequency may be converted (heterodyned) to a fixed intermediate frequency (IF) by mixing it with (i.e., multiplying it by) a signal from a local oscillator (LO) of appropriate frequency. Multiplying two frequencies creates an output containing the sum and difference frequencies. One of these outputs is selected as the IF signal by filtering. The IF signal contains the phase and amplitude information of the original RF signal but at a more convenient (i.e., usually lower) fixed frequency. In frequency-domain heterodyne fluorometry, the RF emission signal is mixed with a second, coherent frequency, and the IF is the isolated difference frequency output. Typically, a gain-modulated detector performs the mixing step.

If the source and detector frequencies are the same in a heterodyning scheme, the method is called homodyning. Homodyning, by definition, results in a zero-frequency (DC) IF signal. The intensity is proportional to the cosine of the difference of the phase between the detector and the emission. To acquire the entire phase and modulation information of the emission signal, the phase difference may be stepped systematically between the source and detector modulation signals. Alternatively, the RF signal may be demodulated using two LO signals whose phases are 90 degrees apart. The two resulting signals, the in-phase (I) and quadrature (Q) signals, are the Cartesian representations of the phase and modulation (cosine and sine components).

Homodyning is commonly used to collect phase-resolved data with a single frequency reference and a fixed phase difference. By properly choosing the phase of the detector, one can suppress or enhance certain lifetimes. A disadvantage of homodyning relative to heterodyning is that homodyning is more affected by DC offsets in the mixing and detection electronics.

The heterodyne frequency-domain method has two significant advantages over time-domain methods: (1) an enhanced excitation duty cycle, and (2) measurement of phase and modulation.

An enhanced excitation duty cycle may be advantageous because it implies that a near maximal amount of luminescence is being excited from the sample. (The excitation duty cycle is the fraction of time that the system is illuminated.) If the illumination is a pure sine wave, the excitation duty cycle can be as large as 50%. However, if the illumination is a narrow pulse, as in multiharmonic phase and modulation fluorometry, the excitation duty cycle will be much lower, comparable to that for time-domain methods.

Measurement of phase and modulation may be advantageous because these quantities may be relatively unaffected by the DC luminescence intensity of the system, or by fluctuations in light source intensity, drift of electronic offsets, and errors in sample concentration. Conversely, intensity measurements, such as those used in time-domain methods, may be strongly affected by these factors, so that they must be corrected by normalization and/or calibration.

Despite these advantages, the heterodyne frequency-domain method has two significant disadvantages, especially relative to time-domain methods: (1) a reduced detection duty cycle, and (2) a low sensitivity.

A reduced detection duty cycle is a significant disadvantage because it reduces the amount of luminescence that is detected. (The detection duty cycle is the fraction of time that the detector can process light.) Typically, the detector is internally gated or gain modulated for the heterodyning step because the detector cannot respond externally to the high-frequency luminescence emission signal. If the luminescence is a pure sine wave, the detected signal optimally will be gated off 50% of the time, either by gating the signal or gating the detector.

A low sensitivity is a significant disadvantage because it requires higher quantities of reagents and/or longer analysis times, if a sample may be analyzed at all. This low sensitivity reflects in part the cumulative effects of dark noise, which becomes an ever larger fraction of the signal as light levels are reduced.

SUMMARY OF THE INVENTION

The invention provides apparatus and methods for determining temporal properties of photoluminescent samples using frequency-domain photoluminescence measurements. These measurements may include photon counting and/or the separation of measured luminescence into potentially overlapping time bins.

BRIEF DESCRIPTION OF THE FIGURES

FIG. 2 is a schematic view of an apparatus for detecting light in accordance with the invention.

DETAILED DESCRIPTION OF THE INVENTION

Figure 1:
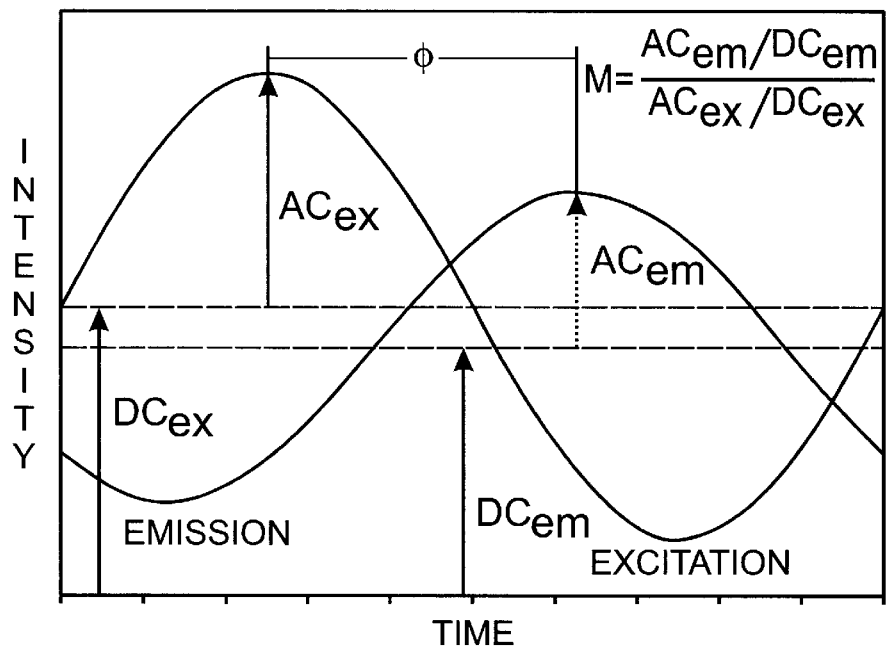
FIG. 1 is a schematic view of a frequency-domain time-resolved measurement, showing the definitions of phase angle (phase) φ and demodulation factor (modulation) M.

The invention provides apparatus and methods for measuring a temporal property of a luminescent sample. The measurements may include (1) illuminating the sample with intensity-modulated incident light, (2) detecting luminescence emitted from the sample in response to the illumination, and (3) determining the temporal property using the measured luminescence. The measurements also may include photon counting and/or the separation of measured luminescence into potentially overlapping time bins. The measurements also may include determination of frequency-domain parameters by counting locked-in photons (CLIP™).

The measurements may involve repeated steps and/or additional steps. For example, the steps of illuminating the sample and detecting luminescence may be performed simultaneously. Moreover, these steps may be performed repeatedly on a single sample for signal averaging before performing the step of determining the temporal property, or they may be performed together with the step of determining the temporal property on a series of samples.

FIG. 2 is a schematic view of an apparatus 50 constructed in accordance with the invention. Apparatus 50 includes a light source 51, a sample channel 52, a frequency source 53, and an optional reference channel 54. Light source 51 is configured to illuminate a sample 56 with intensity-modulated light. Sample channel 52 is configured to detect and analyze light such as photoluminescence transmitted from the sample. Frequency source 53 is configured to generate a frequency, which may be derived from or used to drive the light source, and which may be used to drive components of the sample and reference channels. Optional reference channel 54 is configured to detect light transmitted from the light source, so that the output of the sample channel can be corrected to account for fluctuations and/or other irregularities in the output of the light source.

The sample channel may include a (sample) detector 58a, a discriminator 60a, a count distributor 62a, at least one parallel counter 64a, and an analyzer (or discrete analyzer) 65a. Detector 58a is configured to detect the light transmitted from sample 56 and to convert it to a signal. Discriminator 60a is configured to convert the signal into pulses that correspond to individual detected photons. Count distributor 62a is configured to direct the pulses to a counter corresponding to the phase delay of the photon relative to the excitation signal, based on input from the frequency source. Each counter 64a is configured to tabulate the number of pulses directed to it by the count distributor. Analyzer 65 is configured to determine a temporal property of the sample, based on the detected luminescence. The temporal property may be compute discretely and/or computed in the frequency-domain, for example, by computing a Fourier transform.

The optional reference channel also may include a detector 58b, a discriminator 60b, a count distributor 62b (interfaced with a frequency source), at least one parallel counter 64b, and an analyzer 65a.

The light sources, detectors, and optical relay structures for transmitting light from the light source to the sample (or optional reference detector) and from the sample to the sample photodetector in apparatus 50 collectively comprise a photoluminescence optical system 66. These components are described in detail in a subsequent section entitled "Photoluminescence Optical System." Generally, light source 51 should produce light that is either intensity modulated or capable of being intensity modulated. Examples of suitable light sources include arc lamps, light-emitting diodes (LEDs), and laser diodes. Generally, detectors 58a,b should detect light and convert it to a signal that can be used to count the number of photons in the detected light. Examples of suitable detectors include photon-counting photomultiplier tubes and avalanche photodiodes.

The discriminator converts the output of the photodetector into an output representative of individual detected photons. Here, discriminators 60a,b convert analog pulses created by detectors 58a,b to digital pulses. The discriminator may be selected to create an output signal corresponding only to input signals having amplitudes or other characteristic parameters lying between preselected limits. For example, a lower limit may be set to distinguish individual photon signals from lower-amplitude dark noise. Similarly, an upper limit may be set to distinguish individual photon signals from higher-amplitude noise reflecting instrument anomalies and/or multiple-photon events. Of course, the lower limit may be set to zero and/or the upper limit set to infinity. The discriminator may be a separate component of the sample or reference channel or an integrated part of the detector or count distributor.

The count distributor directs or distributes signals received from the discriminator to one or more counters according to the phase of the incoming signal. The count distributor is interfaced with the frequency source and is described in detail in a subsequent section entitled "Count Distribution Circuit."

The counter or counters tabulate the number of photons that arrive within a "phase bin" corresponding to a particular portion of a period or range of phase delays, based on information input from the count distributor. The phase bins for different counters preferably cover different but overlapping ranges. A single counter may be used to perform heterodyning (or homodyning) operations using integrated photon pulses rather than analog charge, as long as the counter does not cover the entire excitation period. Two or more counters may be used to calculate phase and modulation (as described below) using the high-frequency signal. If two counters are used, some signal will be lost. However, if three or more counters are used, the entire signal may be collected.

Figure 3:
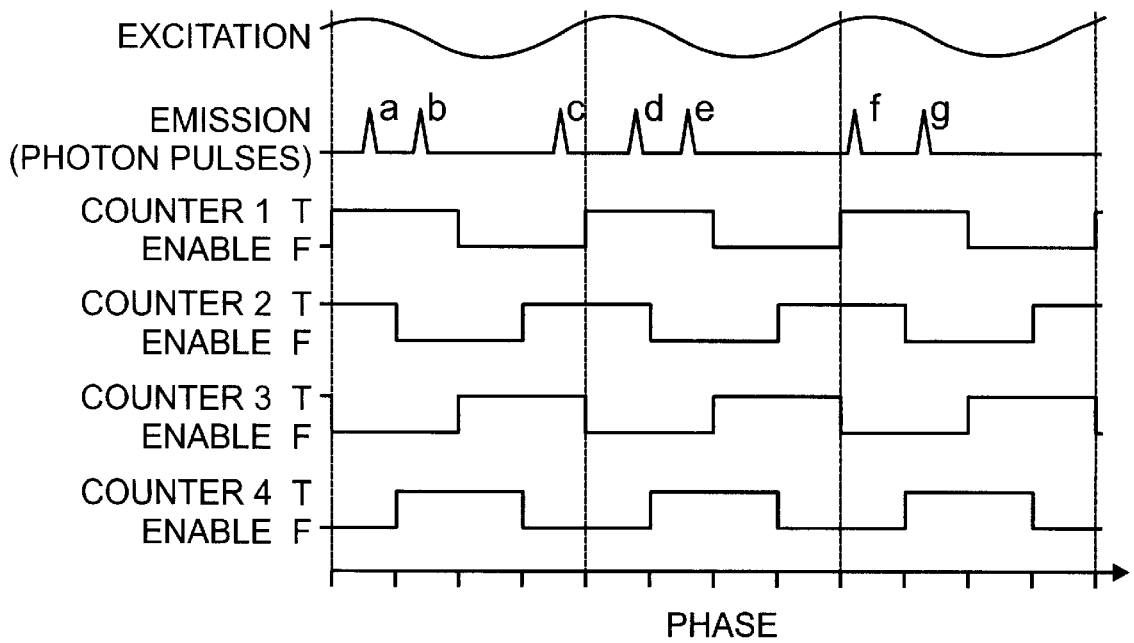
FIG. 3 is a schematic view of a four phase-bin counter system for use in the apparatus of FIG. 2.

FIG. 3 shows a preferred implementation using four counters. Here, each counter captures photons for half a period, and each counter is delayed relative to the previous counter by 90 degrees. The associated phase bins are defined by counter enable signals within the count distributor. Specifically, a photon pulse will be counted by each counter that is enabled when the pulse arrives. In this example, counter 1 will record 6 pulses (a,b,d,e,f,g), counter 2 will record 4 pulses (a,c,d,f), counter 3 will record 1 pulse (c), and counter 4 will record 3 pulses (b,e,g).

Overlapping bins are convenient electronically and may be used to validate system performance. For example, in FIG. 3, each incoming photon will generate a count in two counters, so that the sum of counts in phase bins 1 and 3 should equal the sum of counts in phase bins 2 and 4.

The number of counted photons may be used to compute a frequency-domain quantity, such as phase and/or modulation, by Fourier transforming the numbers into the frequency domain. The Fourier transform can be used to separate harmonics of the excitation signal, which usually are unwanted, if four or more counters are used. The Fourier transform can be performed using a fast Fourier transform (FFT) algorithm to accelerate analysis, if the number of counters is (or can be numerically "padded" to) an integer power of two.

The Fourier transform of the embodiment in FIG. 3 leads to especially simple results. For example, the in-phase component I of the Fourier transform is the difference between the number of photons counted in phase bins 1 and 3 (equivalent to the Fourier cosine transform):

$$I = \theta_1 - \theta_3 \qquad (3)$$

Here, the number of counts in phase bins 1, 2, 3, and 4 is denoted $\theta_1$, $\theta_2$, $\theta_3$, and $\theta_4$, respectively. Similarly, the quadrature component Q of the Fourier transform is the difference between the number of photons counted in phase bins 2 and 4 (equivalent to the Fourier sine transform):

$$Q = \theta_2 - \theta_4 \qquad (4)$$

The phase $\phi$ is the arctangent of the ratio of the quadrature and in-phase components:

$$\phi = \arctan\left(\frac{Q}{I}\right) = \arctan\left(\frac{\theta_2 - \theta_4}{\theta_1 - \theta_3}\right) \qquad (5)$$

The AC amplitude AC is the square root of the sum of the squares of the in-phase and quadrature components:

$$AC = \sqrt{I^2 + Q^2} = \sqrt{(\theta_1 - \theta_3)^2 + (\theta_2 - \theta_4)^2} \qquad (6)$$

The DC amplitude DC is the total number of photons, given by the sum of the number of photons counted in every phase bin:

$$DC = \theta_1 + \theta_3 + \theta_2 + \theta_4 \qquad (7)$$

The DC amplitude also is given by the sum of the number of photons counted in complementary phase bins, e.g., 1 and 3, or 2 and 4. Finally, the modulation M is the ratio of the AC and DC amplitudes:

$$M = \frac{AC}{DC} = \frac{\sqrt{(\theta_1 - \theta_3)^2 + (\theta_2 - \theta_4)^2}}{\theta_1 + \theta_3 + \theta_2 + \theta_4} \qquad (8)$$

The phase and modulation calculated using Equations 5 and 8 are apparent values, not the measured values appearing in Equations 1 and 2. However, the apparent phase and modulation may be "corrected" for instrumental factors giving rise to this difference to yield the measured values, for example, by measuring the apparent phase and modulation for a compound with known lifetime, calculating the correct phase and modulation, and deriving an instrument phase offset and instrument modulation factor. The measured phase will be the difference in the apparent phase and the instrument phase offset. Similarly, the measured modulation will be the product of the apparent modulation and the instrument modulation factor. If the phase bins overlap, Equations 6–8 will include additional normalization constants (for example, overall multiplication factor of ½ for the DC equation). These deviations from the above equations will be corrected with the instrument calibration (modulation factor), so that the additional constants are not strictly required.

The remainder of this section is divided into six sections: (A) count distributor, (B) photon discriminator, (C) photoluminescence optical system, (D) housing, (E) applications to high-throughput screening, and (F) miscellaneous comments. Additional details of an apparatus suitable for implementing features of the invention are shown in U.S. patent application Ser. No. 09/160,533, which is incorporated herein by reference. For example, the apparatus may be under computer or processor control to direct sample handling and/or data collection, among others.

A. Count Distributor

Figure 4A:
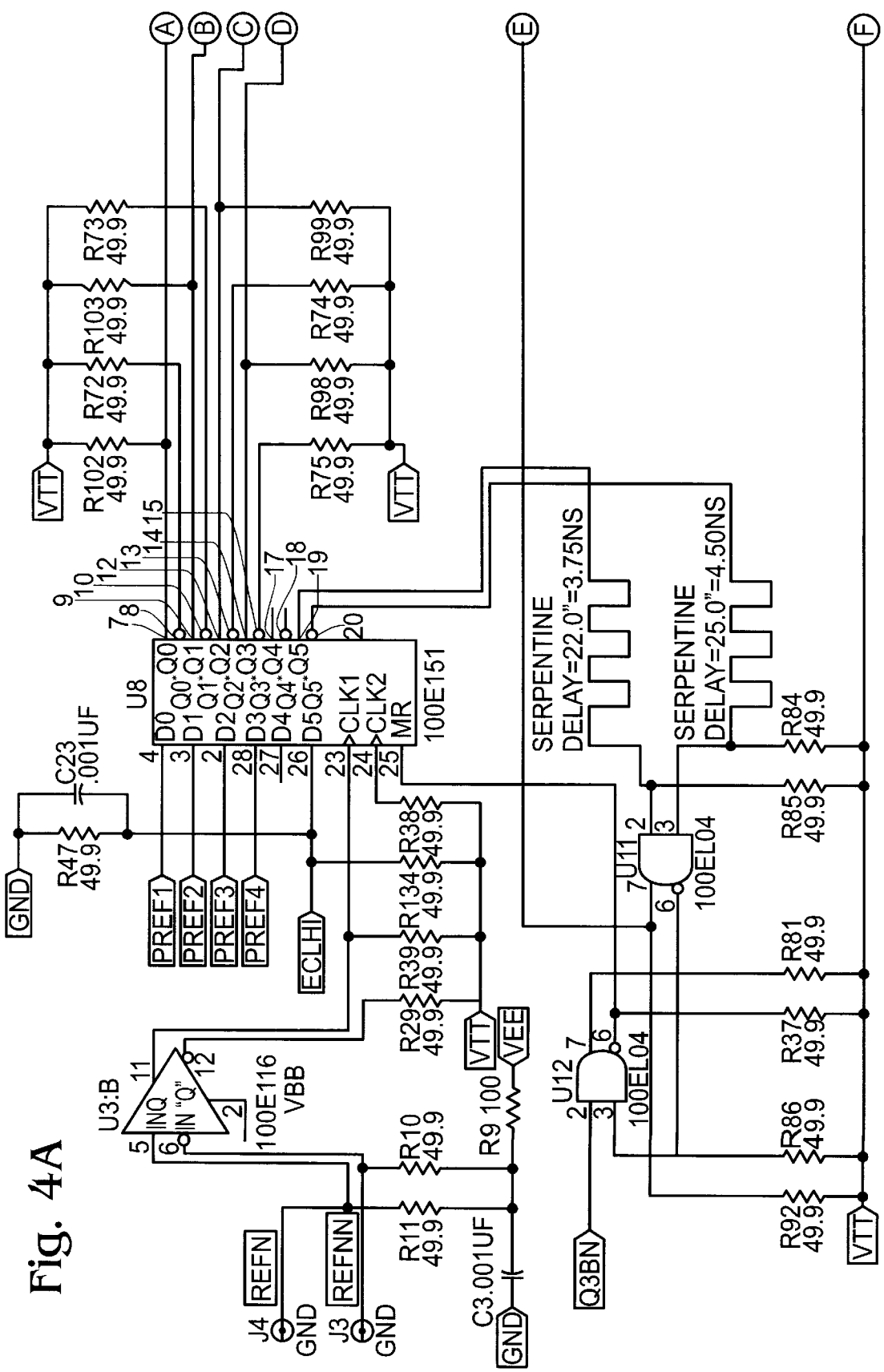
FIG. 4 is a circuit schematic of a count distributor for use in the apparatus of FIG. 2.
Figure 4B:
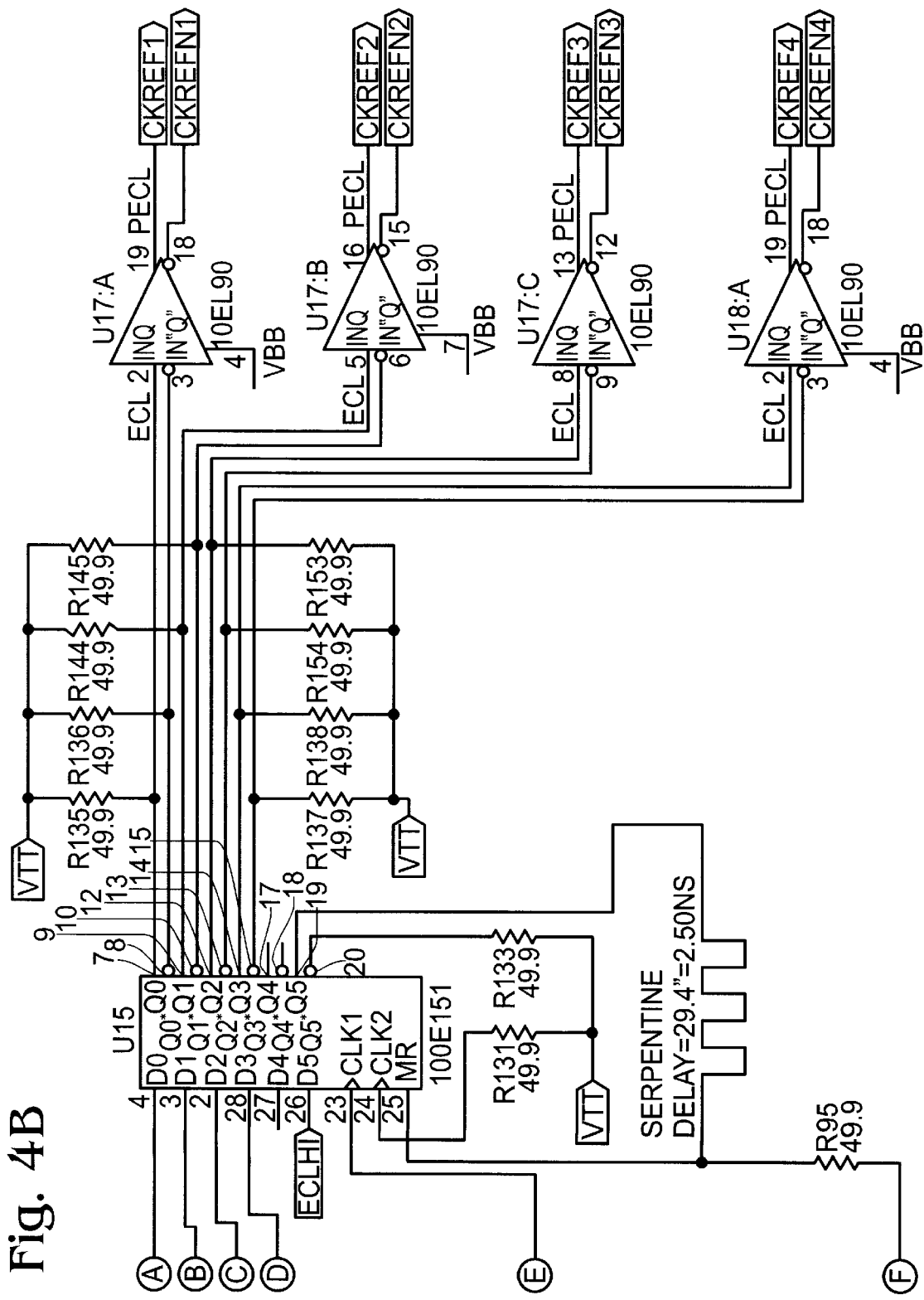

FIG. 4 shows a count distribution circuit for use in the apparatus of FIG. 2. Here, REFIN/REFINN is the differential signal from the discriminator (i.e., the photon pulse), PREF1–PREF4 are the counter enable signals for the four independent counters/phase bins, and CKREF1–CKREF4 are the differential outputs that go to the four counters. Generally, the count distribution circuit directs photon pulses to one or more counters according to the phase of the incoming pulse. The maximum measurable flux rate and the phase resolution of the circuit are determined by its implementation. In the embodiment in FIG. 4, maximum measurable flux rate is determined by the rate at which the circuit processes pulses, and phase resolution is determined by the jitter in the circuit's high-frequency electronics. These and other issues relating to the count distribution circuit are described below.

1. Maximum Average Flux Rate

In the CLIP technique, individual photon pulses and the clock that determines phase are asynchronous. Statistically, the distribution of photons will follow the excitation profile, but individual photons will have no predictable correlation with the excitation. A problem in processing asynchronous signals such as these is metastability of the associated digital electronics. For example, if the two signals arrive at a component without obeying its setup and/or hold times, the component will not output a valid level within the specified propagation delay. To avoid this problem, the two signals can be synchronized using a synchronization circuit. In this way, metastability issues may be handled by the synchronization circuit so that other circuit elements will not be affected by metastability (i.e., so that all setup and hold times will be obeyed).

The synchronization circuit includes two cascaded flip-flops. The second flip-flop is wired to accept the output of the first flip-flop after a preset delay. This delay is long enough for the first flip-flop to settle to a valid state even when the setup or hold times are not met. The embodiment in FIG. 4 includes a 4 nanosecond metastable delay (wait time) so that the associated Motorola™ 100E151 flip-flop will have a mean time between failures of about 130 years (according to the associated Motorola application note AN1504). Generally, the rate of flip-flop failure increases exponentially with decreasing delay. For example, reducing the metastable delay from 4 nanoseconds to 3.8 nanoseconds will decrease the mean time between failures from about 130 years to about 11 years.

The metastability delay sets the pulse pair resolution (PPR) of the count distribution circuit. In particular, while the synchronization circuit is active, no photons can be counted. Ultimately, the PPR limit will be the metastability delay plus a small amount of time to complete a full transition cycle. In the count distribution circuit in FIG. 4, the PPR is limited to about 5 nanoseconds. The preferred embodiment directs the photon pulses into the clock input of the synchronization flip-flop rather than to the data input. In this way, the circuit is able to count multiple photons in during a long on-cycle of a phase bin (high photon flux and low modulation frequency). The number of photons that can be collected during a single on-cycle of a phase bin is only limited by the dead time, and not by the modulation frequency.

2. Phase Resolution

The phase resolution of typical phase and modulation fluorometers is about 0.1 degrees. Analog detection in these fluorometers normally does not permit measurements based on few photons, so that measurements normally are limited by the electronics. The CLIP technique, however, has a phase resolution that is limited primarily by the number of photons and secondarily by the electronic jitter of the phase bins. The number of phase bins does not limit the phase resolution; however, it does contribute to harmonic aliasing.

When the number of photons is small, the statistical uncertainty in the number of counts measured in each phase bin will determine the uncertainty in the Fourier transformed quantities. For example, if the intensities each have an uncertainty of 0.1% ($10^6$ photons collected), the phase uncertainty will be about 0.2% (two times greater than the intensity) or 0.1 degrees (0.002 radians). If the target maximum average flux rate is 10 million counts per second and the target integration time is 100 milliseconds, the maximum expected number of photons measured for a single sample will be about $10^6$. Therefore, the limiting phase resolution will be about 0.1 degrees for high-throughput applications. Higher phase resolutions are achievable by increasing the integration time.

The phase resolution also will be limited by the electronic jitter of the phase bins—the uncertainty in the bin width. In the count distribution circuit in FIG. 4, the expected timing error is about 10 picoseconds. This uncertainty is equivalent to about 1 degree at 300 MHz. At high frequencies, the electronic jitter is expected to be the dominant determinant of the phase resolution of the CLIP technique.

B. Photon Discriminator

FIGS. 5–8 show components of a photon discriminator for use in the apparatus of FIG. 2. Generally, the discriminator converts the output of the photodetector into an output representative of individual detected photons. The performance of the discriminator may be characterized by phase error, dead time, and jitter, which are largely determined by implementation. This section describes a preferred discriminator, which may be termed a high-speed, wide-bandwidth, low-jitter, low-dead-time constant-fraction discriminator.

Phase error is error in assigning a photon to a proper phase bin. To reduce phase error in the measurements, the timing of the pulses from the discriminator should accurately represent the time of arrival of the emitted photons at the photodetector, which (in this embodiment) is a photomultiplier tube (PMT). Two alternative characteristics that reduce phase error are low jitter (high temporal precision) and random timing error (which reduces error by integrating many photons). The simplest approach to timing the photons would be to signal the time when the output amplitude of the photodetector passes a certain threshold (i.e., constant-threshold detection). However, due to variations in the electronic gain of the detector with the wavelength of the photon and the arrival position of the photon on the photoactive area (e.g., the photocathode) of the detector, among other factors, the height of the electrical pulses from the PMT can vary by more than a factor of 5. The peak of the single photon pulse is the most accurate measure of the arrival time of the photon. However, timing the photon pulses with a constant-threshold discriminator will lead to timing jitter just due to the variability in pulse height. A preferred mechanism for maintaining a fixed relationship between the trigger point and the time-of-arrival of the photon that caused the pulse is to use a constant-fraction discriminator. This device measures the arrival time of a photon pulse at a constant fraction of the pulse height.

Dead time is the time after receiving a first photon pulse during which the discriminator is unable to receive a second photon pulse. To reduce dead time, the discriminator should recover from a pulse and be ready for a subsequent pulse as quickly as practical. If successive pulses are not to overlap, the pulses should be very short, which means in turn that the PMT and circuit should be very fast (or, equivalently, have fast rise and fall times).

Jitter is instability of a signal, in terms of phase, amplitude, or both. To reduce jitter, signals should have low electrical noise and high edge rates, since the root-mean-squared (rms) jitter=(rms noise)/(edge slope), where the edge slope is dv/dt. High edge rates again imply fast circuits.

The discriminator preferably should be able to handle both high and low frequency inputs. Because detected emission light may be modulated at frequencies of up to or over about 250 MHz, and because the pulse width from the PMT can be as low as 1.6 nanoseconds, the circuit frequency response should extend up to approximately 1 GHz. Moreover, because the incoming photons may arrive at fewer than 1000 photons/second, the low frequency response should extend down to below about 100 Hz to keep the signal decay of one pulse from overlapping with and changing the trigger location of a following pulse. In the chosen implementation, the constant-fraction discriminator is preceded by a constant-level discriminator, which is sensitive to DC shifts. Additionally, if the circuit has response down to DC, it is possible to determine overload conditions (excessive pulse rate) much more easily. It was therefore decided to extend the low frequency response down to DC.

Figure 5A:
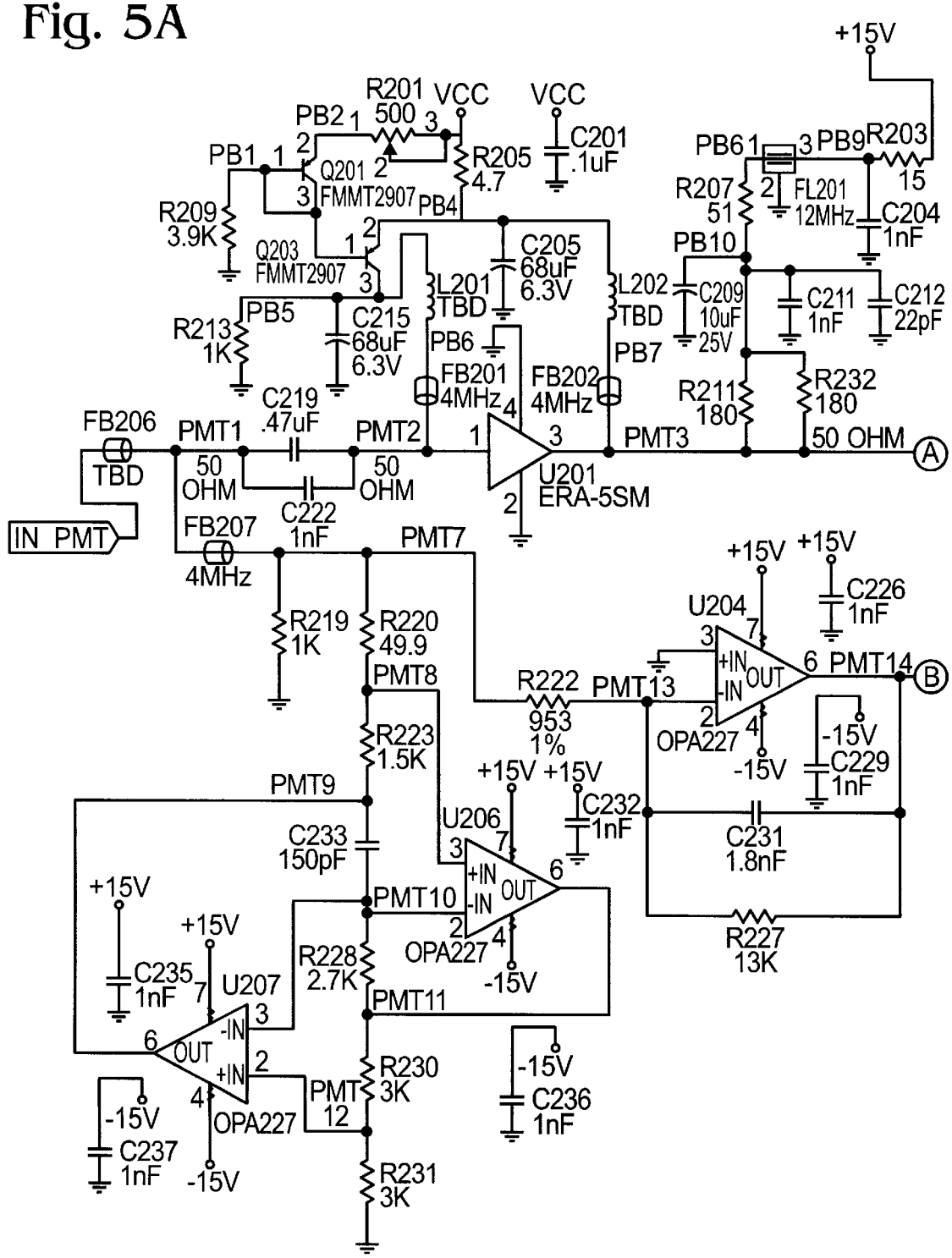
FIG. 5 is a circuit schematic of a preamplifier from a photon discriminator for use in the apparatus of FIG. 2.
Figure 5B:
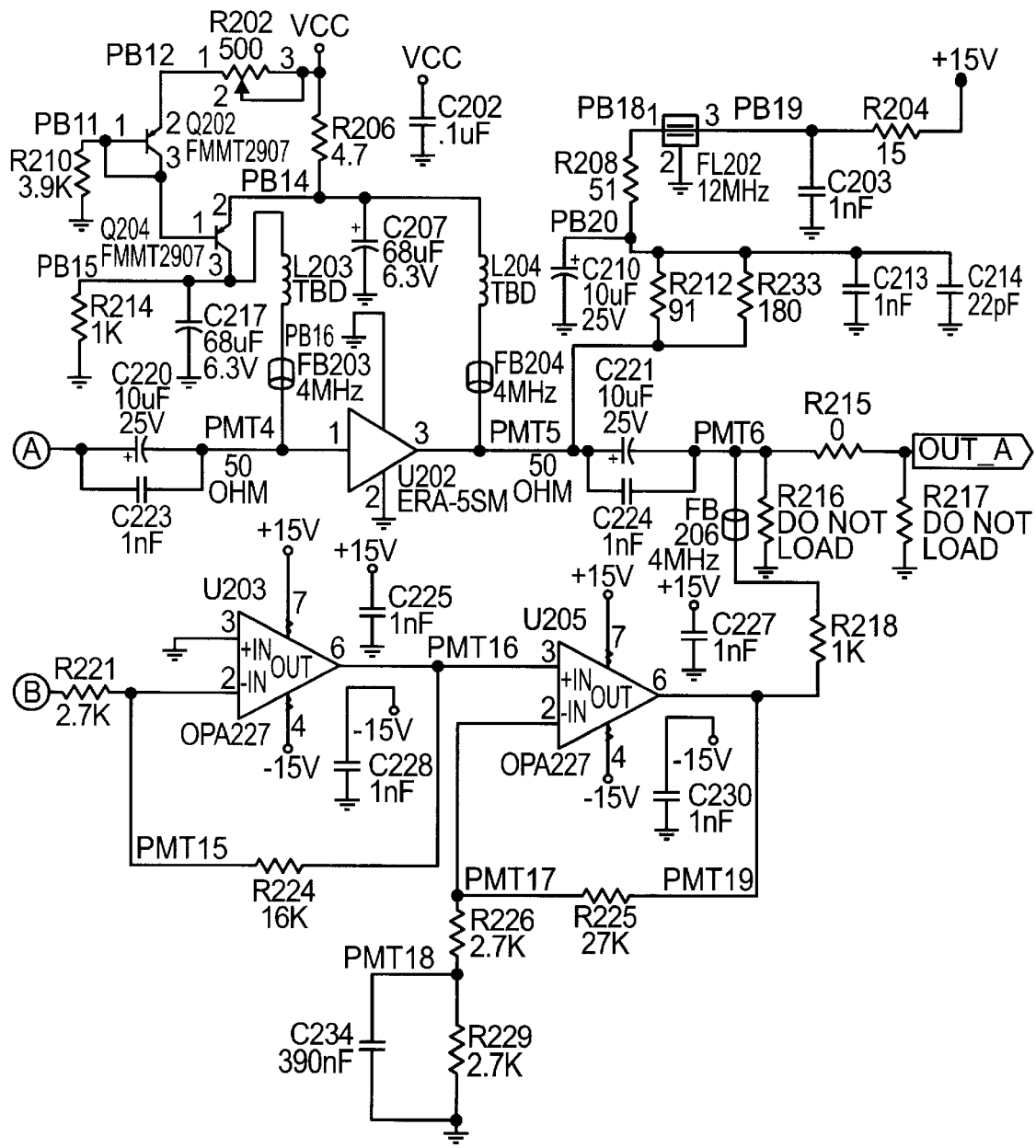

FIG. 5 shows a preamplifier circuit for use in the discriminator. Here, microwave gain blocks (U201, U202) are used to achieve high bandwidth. These gain blocks have a low-frequency cutoff determined by the chosen blocking capacitors. To provide response down to DC, a second circuit path is provided, and the signal is split between the two paths at the input and recombined at the output. To split and recombine the signal while maintaining the pulse shapes, both amplitude and phase response should be uniform across the split. Several features of the circuit maintain this uniformity:

a. The splitter should be first-order so that there are no phase anomalies when the signals are recombined.
b. A split frequency of approximately 10 kHz was chosen. This is low enough that the additional phase shift in the op-amps in the low frequency path (due to finite gain-bandwidth) is small.
c. The interstage and output capacitors in the high-frequency path (C220 and C221) are 20 times the value of the capacitor in the splitter (C219), so that they contribute small amounts of additional phase shift.
d. A gyrator composed of R223, C233, R228, R230, R231, U206 and U207 simulates a 0.6 mH inductor. A real inductor could have multiple self-resonances that would cause serious phase and amplitude disturbances. This simulated inductor combined with R220, C219, C222, and the 50-ohm input impedance of U201 form a first order splitter.
e. The low-frequency path does not receive input from the splitter (because the simulated inductor should be grounded), but rather has a high impedance input (through R222) and a single pole roll-off using C231 and R227.
f. The combining is done after the blocking capacitor of the last gain block, at the input to the next stage (junction of C221, R218, and R215). Since the voltage divider is formed by R218 the output impedance of U202, and the input impedance of the following stage (50 ohms) includes C221, the voltage divider ratio is approximately 40:1 at higher frequencies and 20:1 at lower frequencies (where C221 acts like an open circuit). The network of R226, R229, and C234 compensates for this effect.
g. The gain in both paths is matched. The overall gain is approximately 100.

Figure 6A:
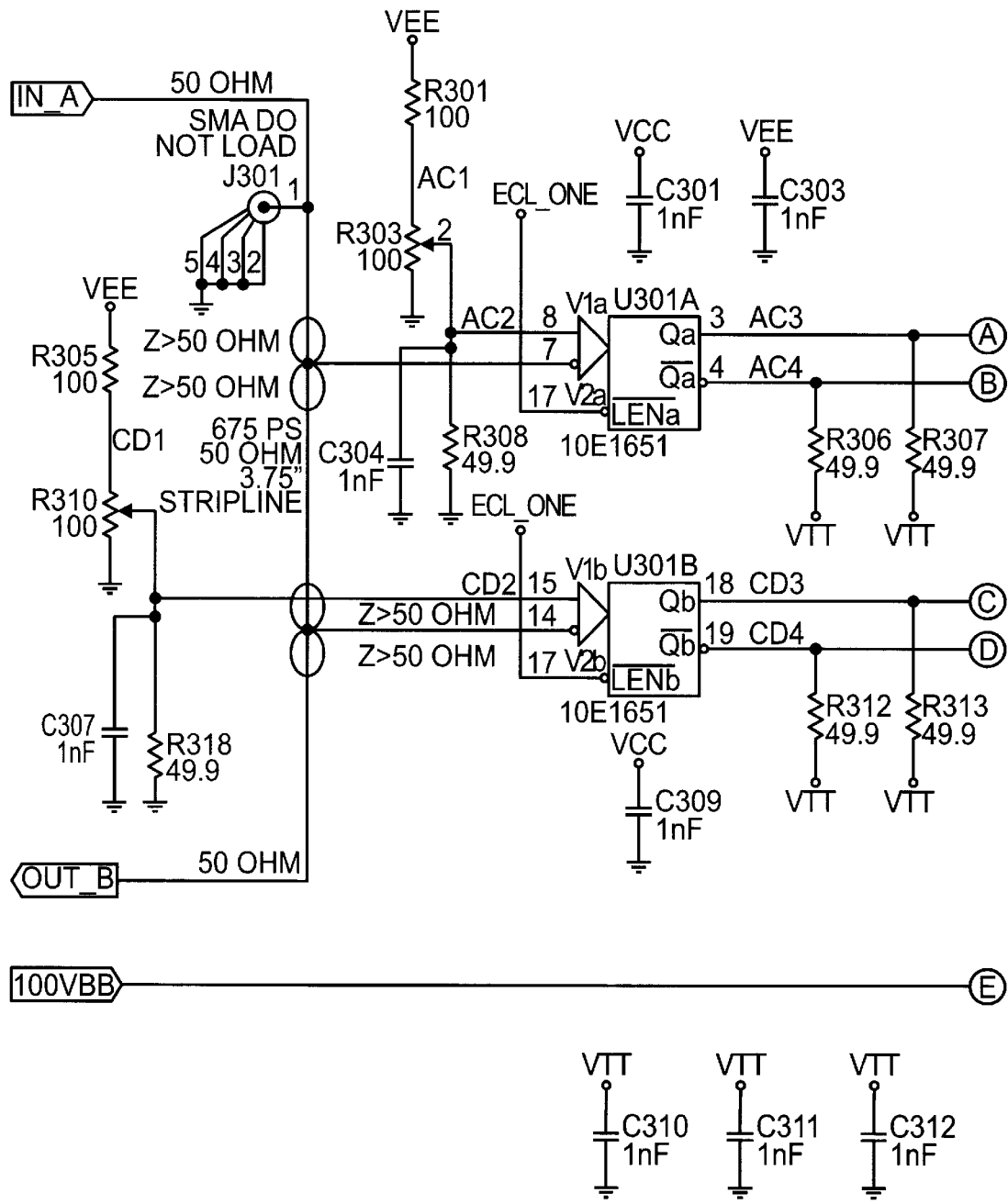
FIG. 6 is a circuit schematic of a constant-level discriminator from a photon discriminator for use in the apparatus of FIG. 2.
Figure 6B:
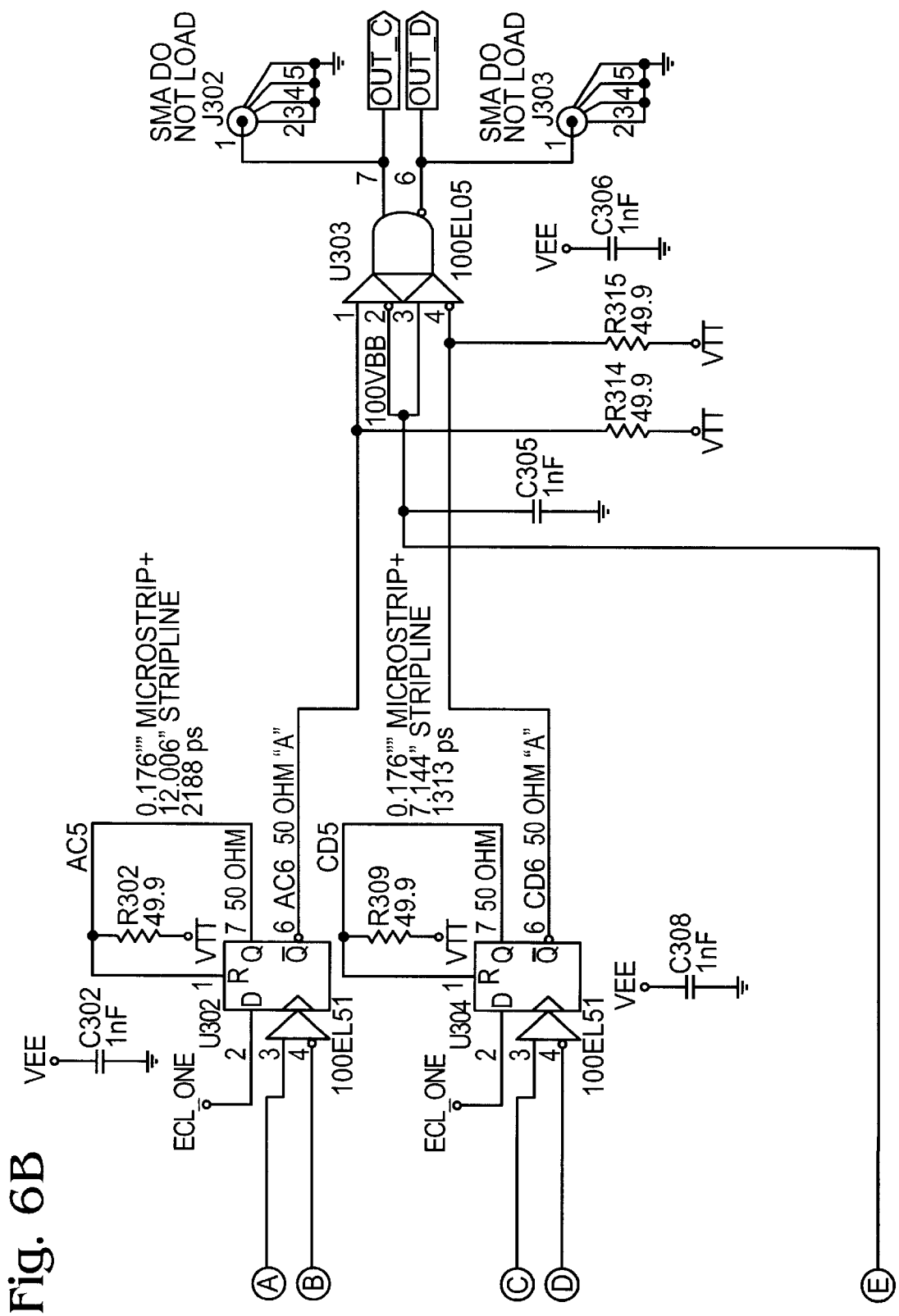

FIG. 6 shows a constant-level discriminator for use in the discriminator. This circuit provides the timing signals for the constant-fraction discriminator (shown in FIG. 7) and eliminates pulses whose amplitude is too high. The basic signal flow is:

a. The pre-amplified pulses (nominal amplitude 500 mV) come in at IN_A on a 50-ohm transmission line. They pass by the (−) input of comparator U301A, continue on past the (−) input of comparator U301B, and then exit to FIG. 7 at OUT_B.
b. When a pulse exceeds the threshold set by R310, U301B sends a differential pulse whose length depends on the pulse amplitude to the clock input of U304. U304 is configured to then create an output pulse whose length is determined by the sum of its gate delay and the length of line CD5. This creates a nominal 1.6 nanosecond pulse, which is sent to U303.
c. When a pulse exceeds the threshold set by R303, U301A sends a differential pulse whose length depends on the pulse amplitude to the clock input of U302. U302 is configured to then create an output pulse whose length is determined by the sum of its gate delay and the length of line AC5. This creates a nominal 2.5 nanosecond pulse, which is sent to U303. The threshold set by R303 is set higher than R310, so that U301A only triggers on "double" pulses (when two pulses have landed on top of each other), which are undesirable because they cannot be accurately timed.
d. Because U301A is triggered before U301B (since the input signal arrives at it 675 picoseconds sooner), and it is longer, if it is triggered, it will produce a pulse that will completely overlap the pulse from U301A. The inputs of U303 are arranged so that if this happens, no pulse will be output from U303, thus eliminating "double height" pulses.
e. Finally, OUT_C and OUT_D form a differential pulse signal of approximately 1.6 nanosecond length, and with a fixed delay from the preamplified PMT output.

Figure 7A:
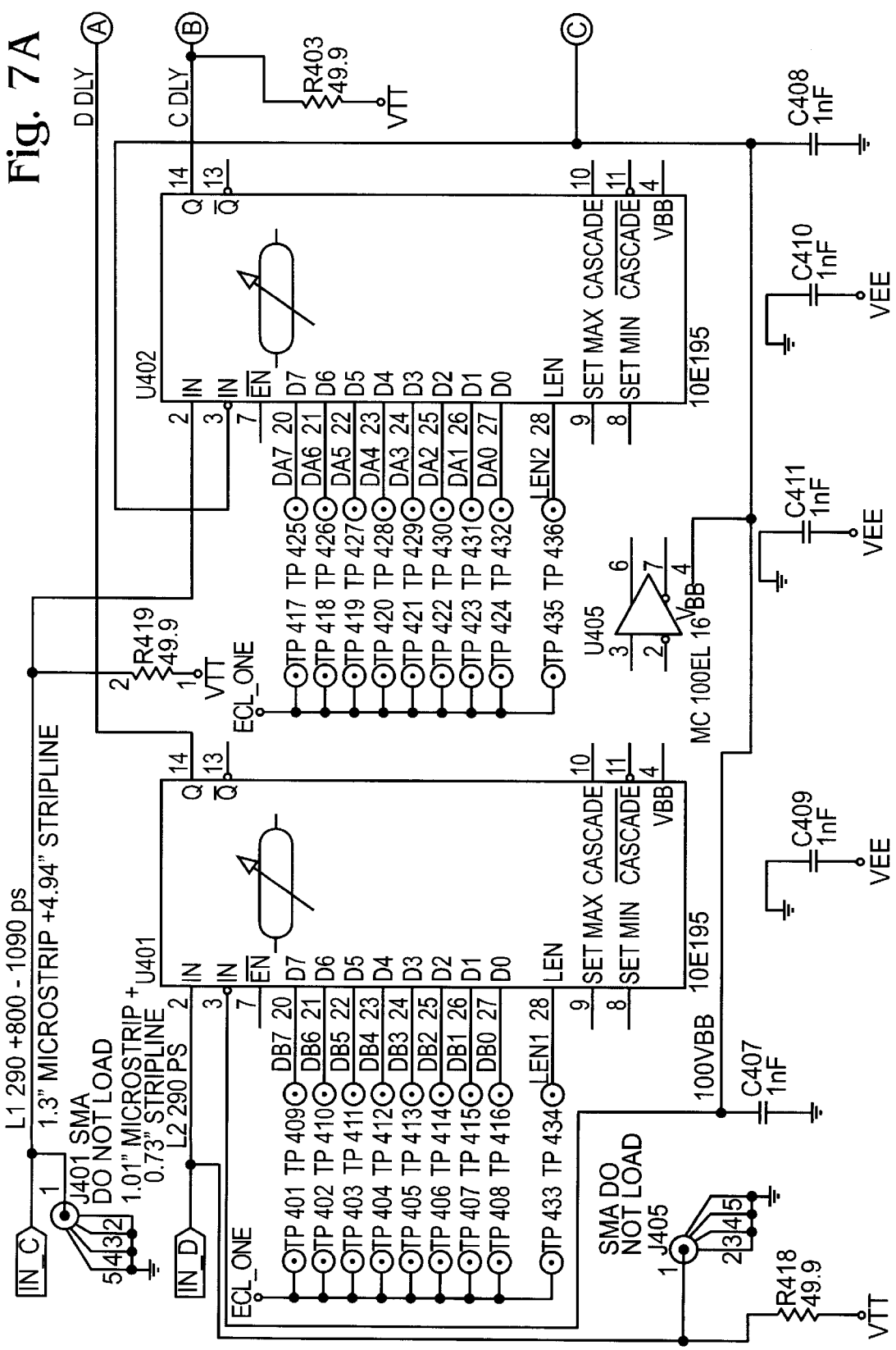
FIG. 7 is a circuit schematic of a constant-fraction discriminator from a photon discriminator for use in the apparatus of FIG. 2.
Figure 7B:
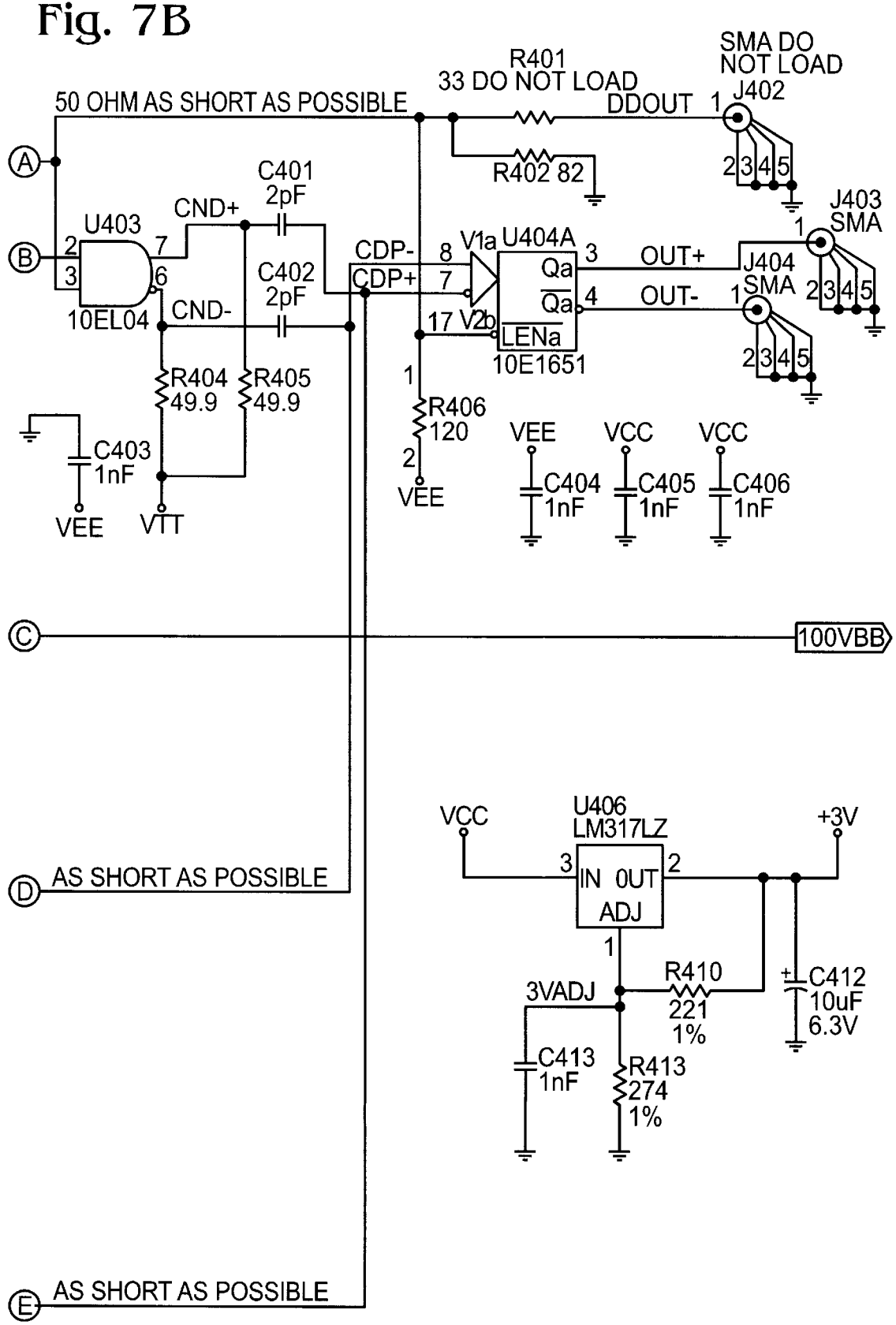
Figure 7C:
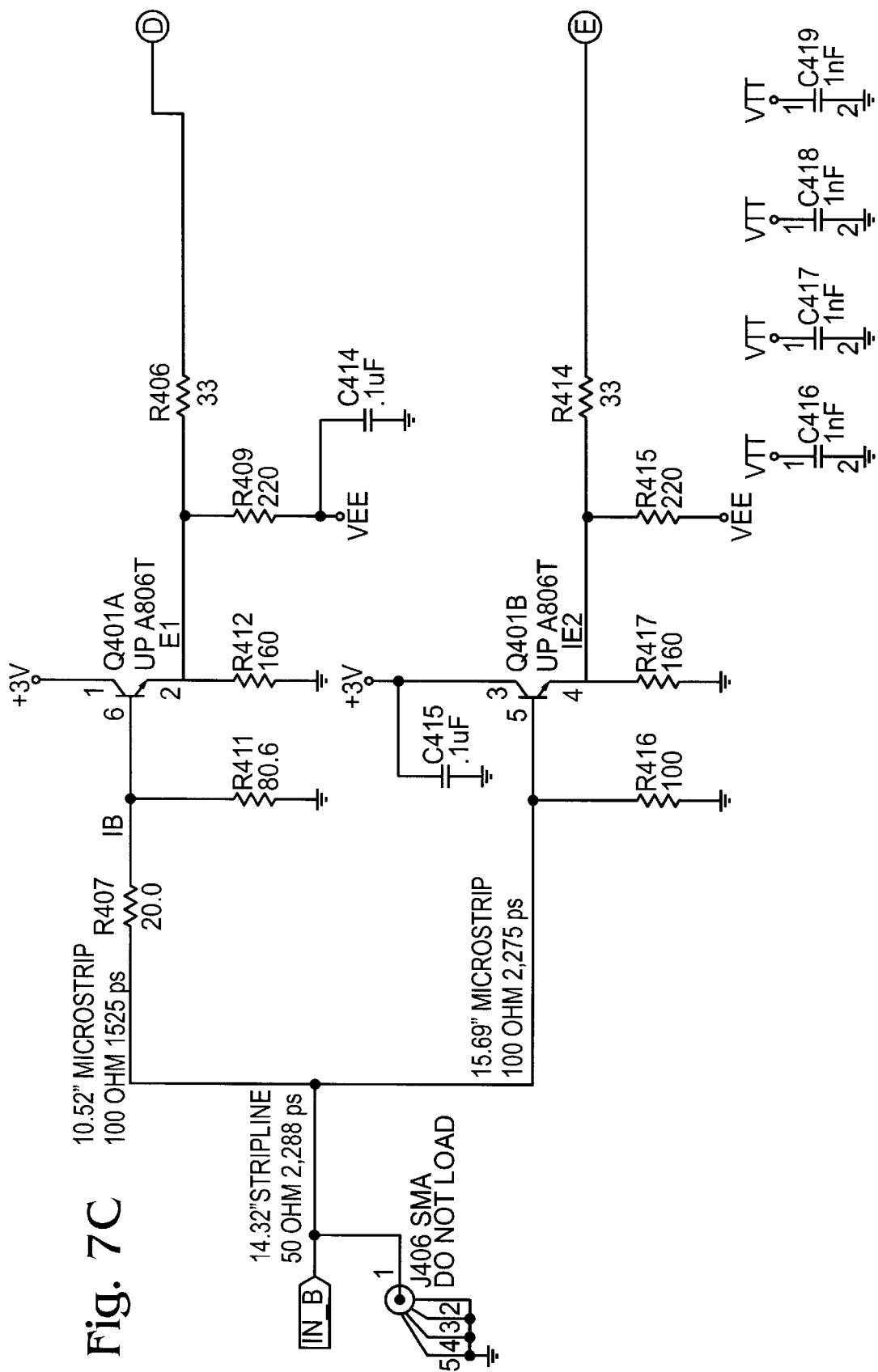
Figure 8:
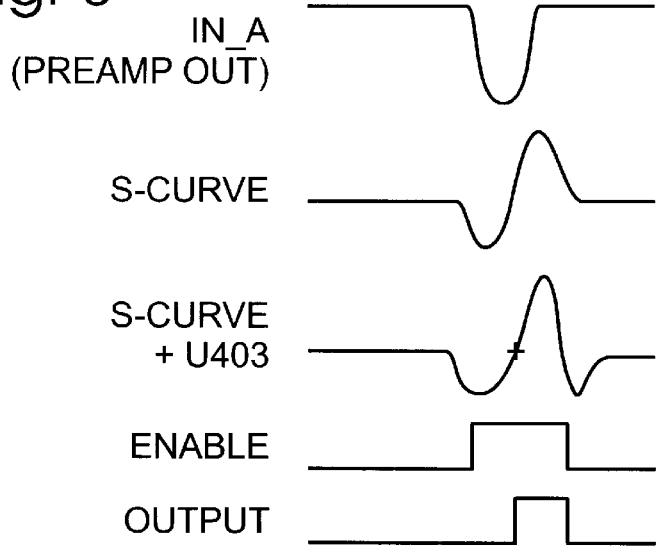
FIG. 8 is a graph of the relative phases of signals associated with a photon discriminator for use in the apparatus of FIG. 2.

FIG. 7 shows a constant-fraction discriminator (CFD) for use in the discriminator. The output signals from the constant-level discriminator are used as gating pulses to the actual constant-fraction discriminator (CFD), determining a window when it is "armed." There are several interesting features of the CFD design:

a. Both signals go through selectable delays (U401 and U402) for fine-tuning of the exact delay relative to the analog signal (OUT_B), as well as the differential delay between C_DLY and D_DLY. In addition D_DLY is inverted.
b. D_DLY is used to enable the constant-fraction discriminator, U404A.
c. The negative-going analog signal (now called IN_B) is split through two different delays, individually attenuated, and buffered by Q401A and Q401B. The difference between these buffered signals is taken by the first stage of the comparator U404A. Because of the relative amplitude and delay, as shown in FIG. 8, an S-curve results, with the zero-crossing at a constant fraction of the input signal.

The comparator trips at the zero-crossing, so this circuit can form a CFD if the comparator is enabled and disabled at the correct times, and the signal state is guaranteed at these times. In other words, the following sequence should occur:

a. The output of the comparator starts low.
b. The negative input of the comparator is above the positive input.
c. The comparator is enabled (no change of state will occur).
d. The positive input of the comparator rises above the negative input. As mentioned in c. above, this is the zero-crossing we seek to detect. This will cause the comparator output to go high.
e. The positive input of the comparator drops below the negative input, causing the comparator output to go low.
f. The comparator is disabled, and we are prepared for step one again.

Conditions 2 and 3 are assured by adjusting the timing such that the D_DLY signal enables the comparator during the initial, negative portion of the S-curve. Condition 4 comes directly from the S-curve. Condition 5 is met by U403 and C401 and 402, which create edges that are timed to drive the comparator inputs in the desired direction. Small capacitors are used to couple the signals in for two reasons: (1) to eliminate any DC effects that could shift the threshold, and (2) to make sure any DC effects die away quickly enough that they do not affect the next pulse to be counted. Condition 6 is assured by correct adjustment of the timing of the U403-C401-C402 edges and the trailing edge of the D_DLY signal. The gate delays and transmission line lengths are comparable to the desired delays and pulse widths, so they should be taken into account in design.

C. Photoluminescence Optical System

Figure 9:
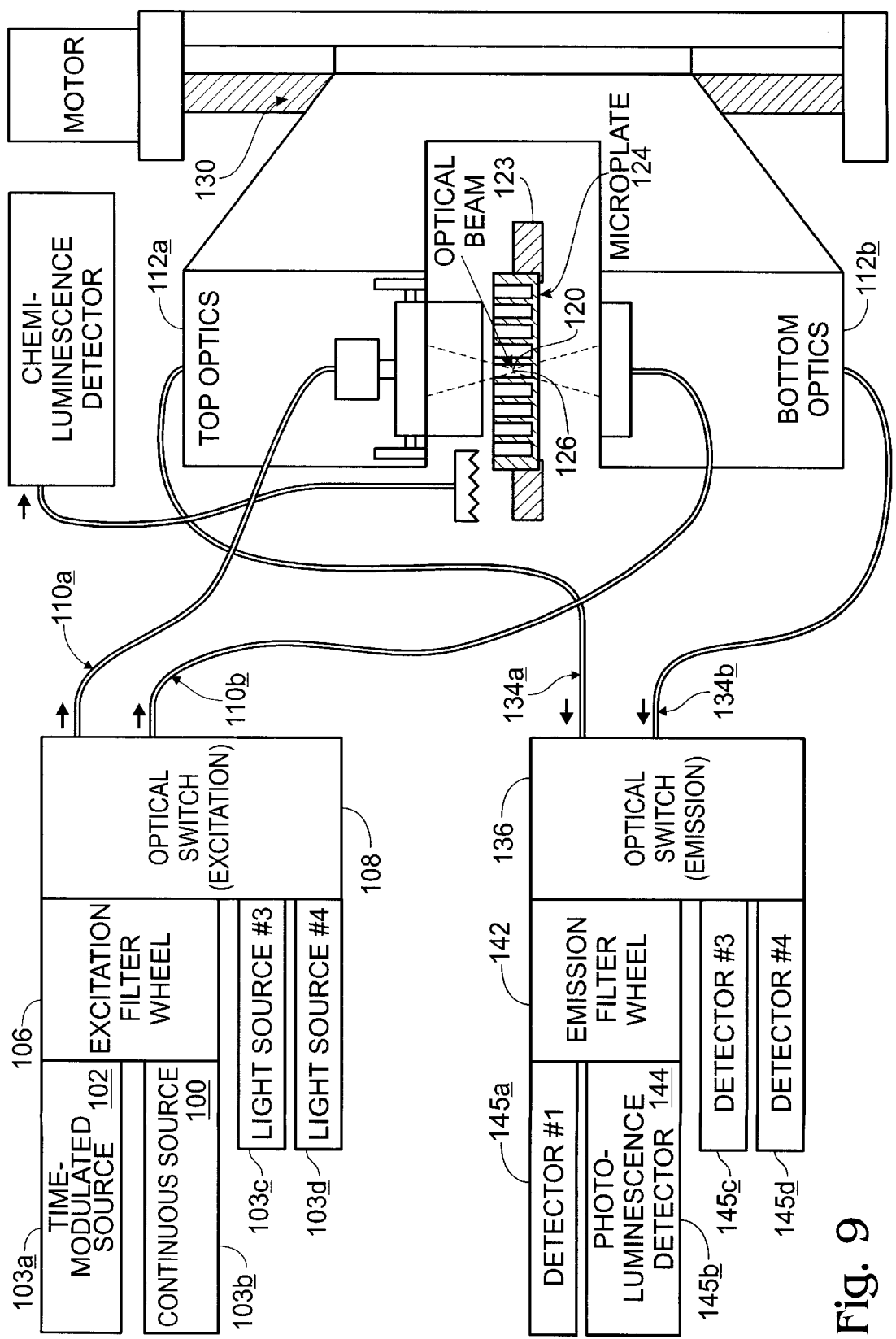
FIG. 9 is a schematic view of a photoluminescence optical system for use in the apparatus of FIG. 2.
Figure 10:
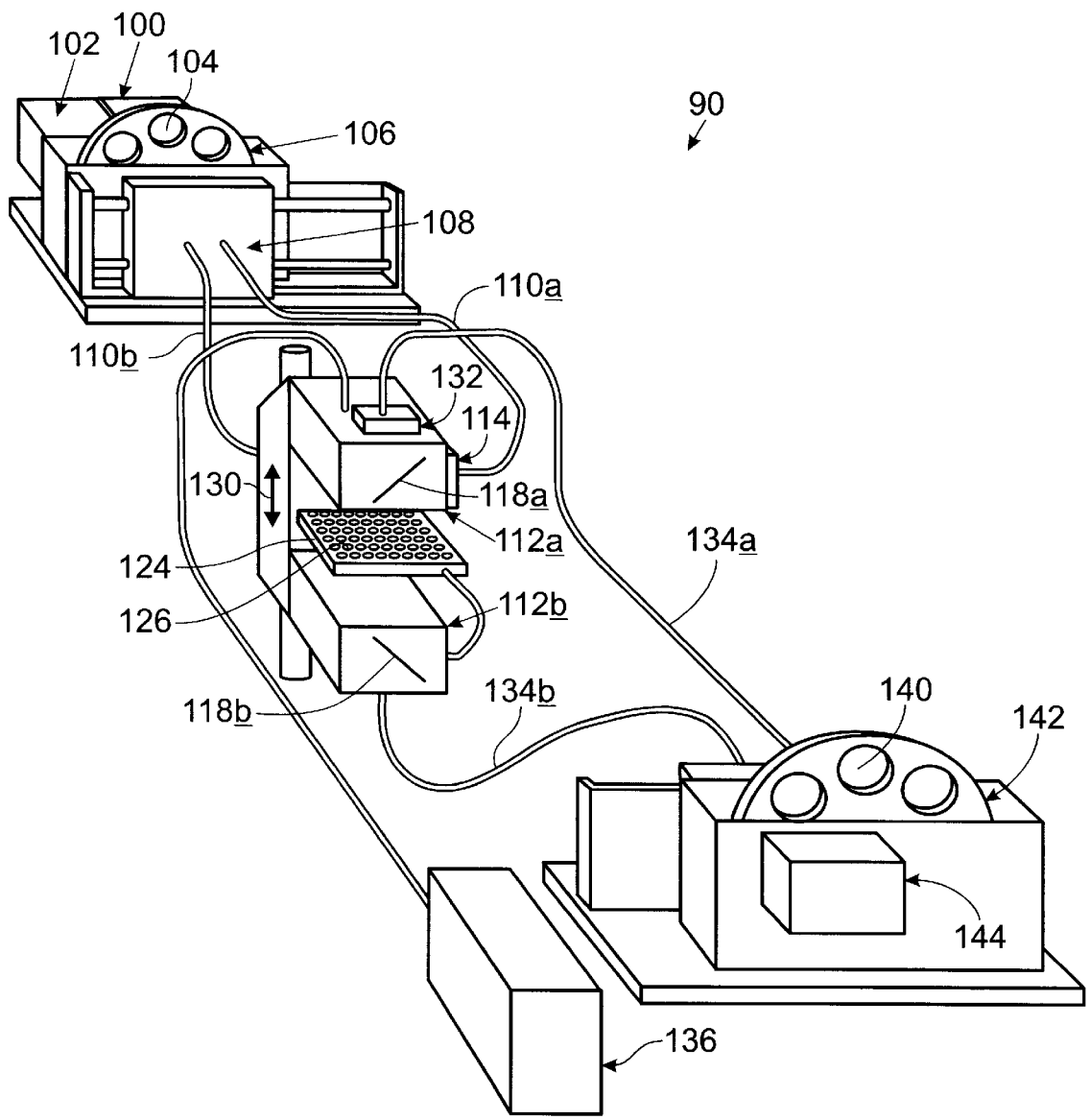
FIG. 10 is a partially schematic perspective view of the system of FIG. 9.
Figure 11:
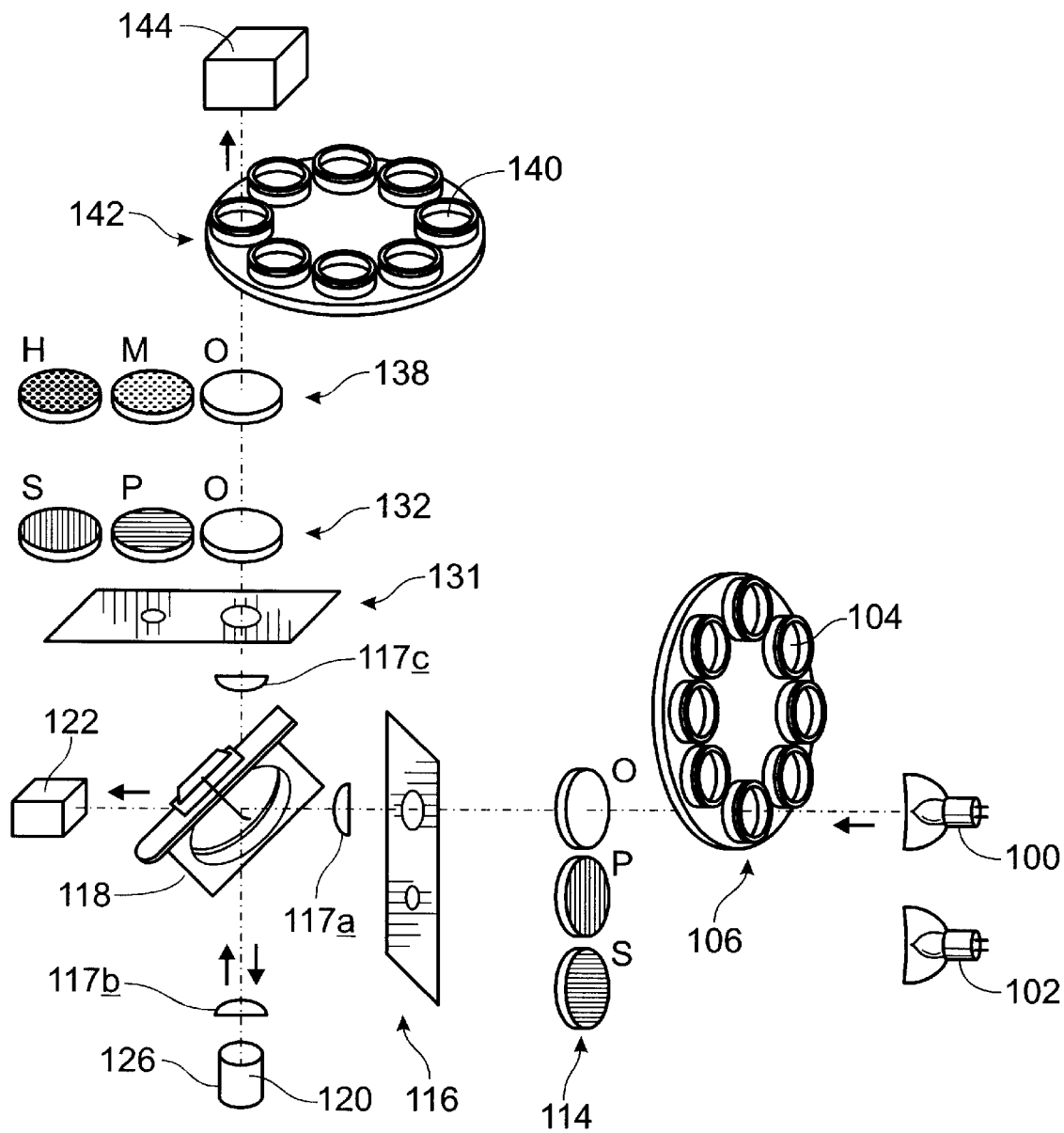
FIG. 11 is a schematic view of optical components from the system of FIG. 9.

FIGS. 9–11 show a photoluminescence optical system 90 for use in the apparatus of FIG. 2. This system may be used to illuminate a sample. This system also may be used to detect light transmitted from a sample before, during, and/or after illumination, and to convert the detected light to a signal that can be analyzed by a sample channel. This system also may be used to detect light output from a light source and to convert the detected light to a signal that can be analyzed by an optional reference channel.

The photoluminescence optical system may include a variety of components, some or all of which may be used in any given assay. These components may include (1) a stage for supporting a sample, (2) one or more light sources for delivering light to the sample, (3) one or more detectors for receiving light transmitted from the sample and converting it to a signal, and (4) optical relay structures for relaying light between the light source, composition, and detector. These components may be chosen to optimize sensitivity and dynamic range, for example, by choosing components with low intrinsic luminescence. These components may be operatively connected to components of the sample and/or reference channels.

The photoluminescence optical system may be used to conduct a variety of steady-state and time-resolved luminescence assays. Steady-state assays measure luminescence under constant illumination, using the continuous light source. Time-resolved polarization assays measure luminescence as a function of time under time-varying illumination, using either the continuous light source, with its intensity appropriately modulated, or the time-varying light source.

Optical system 90 includes a continuous light source 100 and a time-modulated light source 102. Optical system 90 includes light source slots 103a–d for four light sources, although other numbers of light source slots and light sources also could be provided. Light source slots 103a–d function as housings that may surround at least a portion of each light source to provide at least partial protection from radiation or explosion. The direction of light transmission through the incident light-based optical system is indicated by arrows.

Continuous source 100 provides light for absorbance, photoluminescence, and scattering assays, among others. Continuous light source 100 may include arc lamps, incandescent lamps, fluorescent lamps, electroluminescent devices, lasers, laser diodes, and LEDs, among others. Optical system 90 may include a modulator mechanism configured to vary the intensity of light incident on the composition without varying the intensity of light produced by the light source.

A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the duty cycle of the flash source, increasing sensitivity and reducing read times.

Another preferred continuous light source is a NICHIA-brand bright-blue LED (Model Number NSPB500; Mountville, Pa.), which may be used with analytes absorbing blue light.

Time-modulated source 102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a suitable optical modulator. Intrinsically modulated continuous light sources are especially well suited for frequency-domain measurements in that they are generally easier to operate and more reliable.

If the light source must be extrinsically modulated, an optical modulator may be used. The optical modulator generally includes any device configured to modulate incident light. The optical modulator may be acousto-optical, electro-optical, or mechanical, among others. Suitable modulators include acousto-optical modulators, Pockels cells, Kerr cells, liquid crystal devices (LCDs), chopper wheels, tuning fork choppers, and rotating mirrors, among others. Mechanical modulators may be termed "choppers," and include chopper wheels, tuning fork choppers, and rotating mirrors, among others, as described in PCT Patent Application No. PCT/US99/16287, which is incorporated herein by reference.

In optical system 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. For example, a spectral filter may be used to block the red edge of the broad-spectrum light produced by the blue LED described above. In optical system 90, spectrum is altered by an excitation interference filter 104, which preferentially transmits light of preselected wavelengths and preferentially absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers and laser diodes, which output light of only a single wavelength. Therefore, excitation filter wheel 106 may be mounted in the optical path of some light source slots 103a,b, but not other light source slots 103c,d. Alternatively, the filter wheel may include a blank station that does not affect light passage.

Light next passes through an excitation optical shuttle (or switch) 108, which positions an excitation fiber optic cable 110a,b in front of the appropriate light source to deliver light to top or bottom optics heads 112a,b respectively. Light is transmitted through a fiber optic cable much like water is transmitted through a garden hose. Fiber optic cables can be used easily to turn light around comers and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filters," which generally comprise any mechanism for altering the polarization of light. Excitation polarization filters may be included with the top and/or bottom optics head. In optical system 90, polarization is altered by excitation polarizers 114, which are included only with top optics head 112a for top reading; however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light, where polarizations are measured relative to the beamsplitter. Excitation polarizers 114 also may include a standard or ferro-electric liquid crystal display (LCD) polarization switching system. Such a system may be faster than a mechanical switcher. Excitation polarizers 114 also may include a continuous mode LCD polarization rotator with synchronous detection to increase the signal-to-noise ratio in polarization assays. Excitation polarizers 114 may be incorporated as an inherent component in some light sources, such as certain lasers, that intrinsically produce polarized light.

Light at one or both optics heads also may pass through an excitation "confocal optics element," which generally comprises any mechanism for focusing light into a "sensed volume." In optical system 90, the confocal optics element includes a set of lenses 117a–c and an excitation aperture 116 placed in an image plane conjugate to the sensed volume, as shown in FIG. 11. Aperture 116 may be implemented directly, as an aperture, or indirectly, as the end of a fiber optic cable. Preferred apertures have diameters of 1 mm and 1.5 mm. Lenses 117a,b project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120.

Beamsplitter 118 is used to direct excitation or incident light toward the sample and light monitor, and to direct light leaving the sample toward the detector. The beamsplitter is changeable, so that it may be optimized for different assay modes or compositions. In some embodiments, switching between beamsplitters may be performed manually, whereas in other embodiments, such switching may be performed automatically. Automatic switching may be performed based on direct operator command, or based on an analysis of the sample by the instrument. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the sample to the detector.

If one or a few related photoactive molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

Light monitor 122 is used to correct for fluctuations in the intensity of light provided by the light sources. Such corrections may be performed by reporting detected intensities as a ratio over corresponding times of the luminescence intensity measured by the detector to the excitation light intensity measured by the light monitor. The light monitor also can be programmed to alert the user if the light source fails. A preferred light monitor is a silicon photodiode with a quartz window for low autoluminescence.

The sample (or composition) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be extrinsic to the instrument.

The sample holder can include microplates, biochips, or any array of samples in a known format. In optical system 90, the preferred sample holder is a microplate 124, which includes a plurality of microplate wells 126 for holding compositions. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle of about 15–35 degrees and a minimum diameter of about 0.1–2.0 mm. A preferred cone angle is about 25 degrees. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in PCT Patent Application Ser. No. PCT/US99/08410, which is incorporated herein by reference.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In optical system 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 9 and 10. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In optical system 90, epi modes are supported, so the excitation and emission light travel the same path in the optics head, albeit in opposite or anti-parallel directions. However, trans modes also can be used with additional sensors, as described below. In optical system 90, top and bottom optics heads move together and share a common focal plane. However, in other embodiments, top and bottom optics heads may move independently, so that each can focus independently on the same or different sample planes.

Generally, top optics can be used with any sample holder having an open top, whereas bottom optics can be used only with sample holders having optically transparent bottoms, such as glass or thin plastic bottoms. Clear bottom sample holders are particularly suited for measurements involving analytes that accumulate on the bottom of the holder.

Light is transmitted by the composition in multiple directions. A portion of the transmitted light will follow an emission pathway to a detector. Transmitted light passes through lens 117c and may pass through an emission aperture 131 and/or an emission polarizer 132. In optical system 90, the emission aperture is placed in an image plane conjugate to the sensed volume and transmits light substantially exclusively from this sensed volume. In optical system 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In optical system 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In optical system 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and diffractive beam splitters (e.g., acousto-optic modulators), which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In optical system 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, photoluminescence, and scattering assays. In optical system 90, there is one detector 144, which detects light from all modes. A preferred detector is a photomultiplier tube (PMT). Optical system 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT Patent Application Ser. No. PCT/US99/03678, which is incorporated herein by reference.

D. Housing

Figure 12:
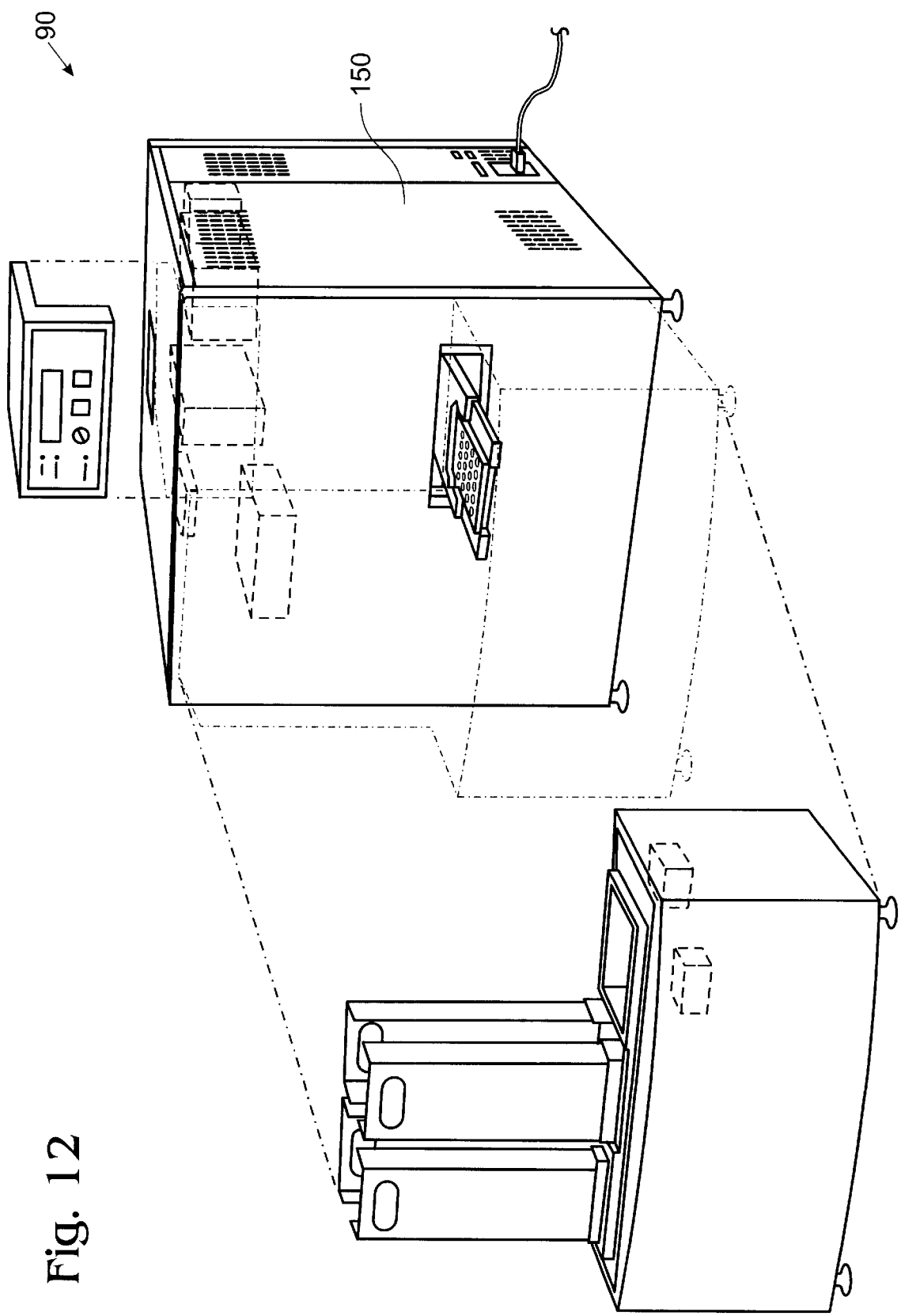
FIG. 12 is a partially exploded perspective view of a housing for use in the apparatus of FIG. 2.

FIG. 12 shows a housing 200 and other accessories for use in the apparatus of FIG. 2. Housing 200 substantially encloses the apparatus, forming (together with light source slots 103a–d) two protective layers around the continuous high color temperature xenon arc lamp. Housing 200 permits automated sample loading and switching among light sources and detectors.

E. Applications to High-Throughput Screening

High-throughput screening (HTS) is used to search large libraries of compounds for compounds that will interact effectively with a target. These few compounds may then be used as leads for further analysis on the road to drug discovery. Recently, the number of library compounds and targets for screening has increased dramatically. In particular, the number of library compounds is now in the hundreds of thousands. This increase in number and the concomitant need to improve screening throughput have led to a need for industrial-strength analytical methods with a low cost per assay.

HTS assays should satisfy three primary criteria. First, HTS measurements should be rapid. To screen libraries containing hundreds of thousands of compounds, the measurement time per sample should be small (less than 100 milliseconds), and the number of replicates, controls, and background samples should be a minimum.

Second, HTS measurements should be inexpensive, because the cost of each assay must be multiplied by the typically significant number of such assays that must be performed. To reduce reagent costs, required amounts of library compounds should be kept to a minimum. Thus, HTS apparatus and methods should be capable of detecting low concentrations of compound. For example, in HTS binding assays, a low label concentration is about 0.5 nanomolar, which is primarily determined by binding affinity.

Third, HTS measurements should be precise (low error), accurate (small deviations from correct values), and robust (insensitive to common interferences). Robustness is particularly important, especially as assay volume is reduced, because interferences can cause a high false hit rate. Typical hit rates for well-designed assays may be less than about 1% of the compounds tested, whereas false hit rates may be several percent. All hits (true or false) must be sent on to secondary screening to determine which are actual leads.

The apparatus and methods provided by the invention may satisfy some or all of these HTS criteria. For example, photon-counting frequency-domain measurements can be used at low light levels due to their enhanced sensitivity, which may reduce reagent requirements. Moreover, photon-counting frequency-domain measurements can be relatively insensitive to dark noise, background luminescence, scattering, absorption, and/or quenching, which may improve precision, accuracy, and robustness.

The apparatus and methods provided by the invention can be used with apparatus, methods, and compositions described in the above-identified patent applications, which are incorporated herein by reference. For example, the apparatus and methods can be used with high-sensitivity luminescence apparatus and methods, including those described in U.S. patent application Ser. No. 09/062,472, filed Apr. 17, 1998, U.S. patent application Ser. No. 09/160,533, filed Sep. 24, 1998, PCT Patent Application Ser. No. PCT/US98/23095, filed Oct. 30, 1998, and PCT Patent Application Ser. No. PCT/US99/01656, filed Jan. 25, 1999. The apparatus and methods also can be used with sample holders designed for performance with the above-identified high-sensitivity luminescence apparatus and methods, including those described in PCT Patent Application Ser. No. PCT/US99/08410, filed Apr. 16, 1999. These sample holders may reduce the required amount of reagent (or library compound) per assay by using a smaller volume. A well in a typical 96-well HTS plate can hold 300 microliters, with typical assay volumes lying between 100 and 200 microliters. In contrast, a well in a 1536-well high-density HTS plate can hold up to 10 microliters, with low-volume assays using 5 microliters or less. Consequently, apparatus and methods that permit screening with low-volume samples may lead to 95% or greater reductions in reagent cost.

F. Miscellaneous Comments

The apparatus and methods provided by the invention may have several advantages over standard frequency-domain methods, reflecting in part (1) photon-counting detection, (2) enhanced detection duty cycle, and/or (3) intrinsic measurement of phase and modulation.

Photon counting is the digital tabulation of the number of detected photons, in contrast to the analog integration of a current resulting from the detection of photons. Photon counting may reduce dark noise by counting higher-level pulses corresponding to individual photons but ignoring lower-level signals corresponding to dark current that would otherwise contribute to an integrated analog signal. The use of photon counting in the invention may improve sensitivity by a factor of two or more, relative to standard (i.e., analog) frequency-domain methods.

Detection duty cycle is the fraction of time that the detector can process a photon. A high detection duty cycle may improve speed and resolution, because the detector will be available to detect a higher fraction of the transmitted light. The use of ungated (i.e., always on) detection in the invention increases the detection duty cycle to about 100%, in contrast to the use of gated detection in the standard heterodyne method, which reduces the detection duty cycle to less than about 50%.

The intrinsic measurement of phase and modulation provides a more robust signal than provided by standard frequency-domain methods, which rely on intermediate measurements of intensities. Such intrinsic measurement may be accomplished using a direct single-frequency lock-in. A single frequency may be used for both excitation and detection. The use of a single oscillator is a significant practical improvement, because it is easier to implement than the two phase-locked frequency sources required for heterodyne fluorometry. The CLIP method measures phase and modulation without heterodyning or traditional homodyning. Moreover, the outputs may be digital and therefore not subject to the DC noise and drift that can accompany homodyne fluorometry.

The apparatus and methods provided by the invention also may share the advantages of standard frequency-domain methods over time-domain methods, reflecting in part enhanced excitation duty cycle. The excitation duty cycle is the fraction of time that the system is illuminated. The use of sinusoidal excitation as described here increases the excitation duty cycle to about 50%, in contrast to the pulse excitation in time-domain methods that reduces the excitation duty cycle to less than about 0.1%.

Figure 13:
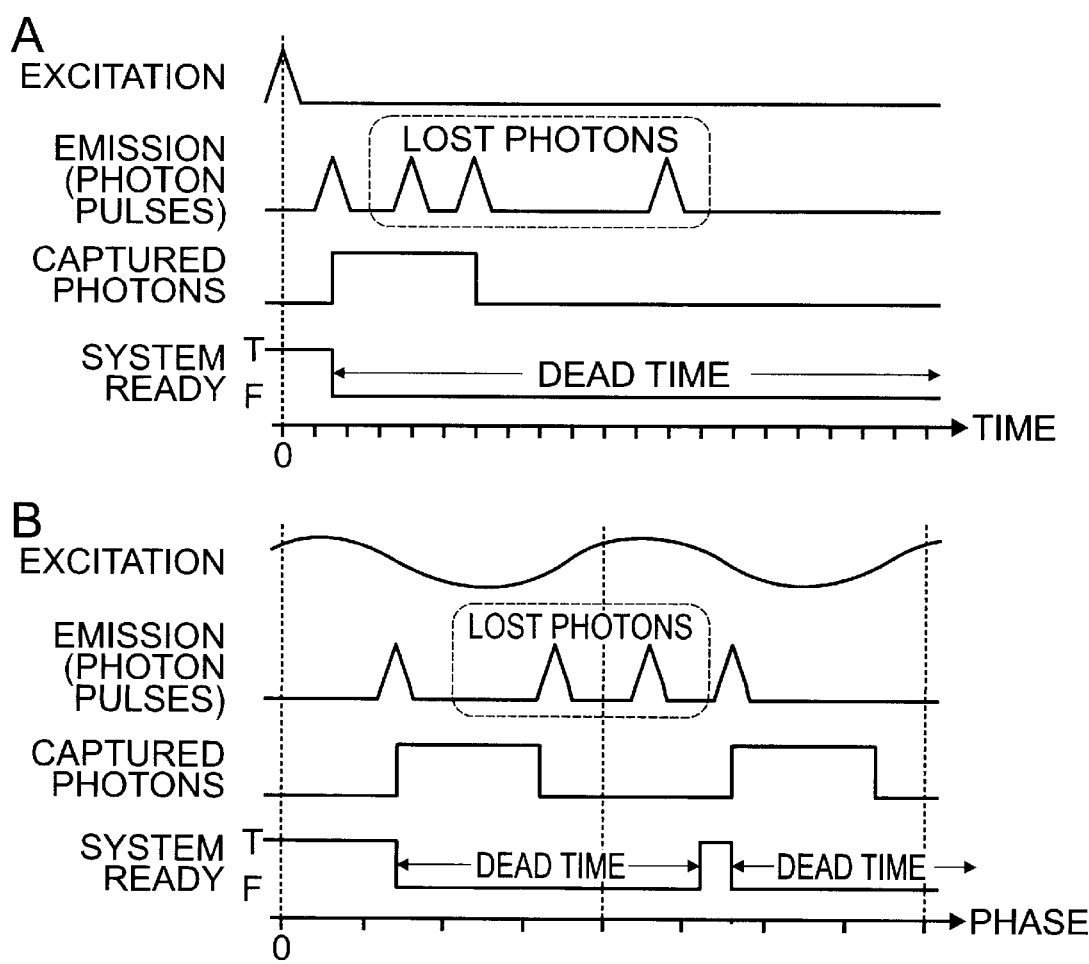
FIG. 13 is a schematic view of time-domain and frequency-domain measurements, showing how detector dead time affects lost photon pulses in the two techniques.

The apparatus and methods provided by the invention also have one primary disadvantage: a limited maximum flux rate. The maximum flux rate is the maximum number of photons that can be detected per unit time. The maximum flux rate is determined by the electronic pulse-pair resolution (PPR) and the probability of receiving a second photon within the detector dead time. The PPR is the minimum time between impinging photons required for the signal from the photons to be just resolvable by the apparatus as arising from two photons. The detector dead time is a period after detection of a photon during which the detector cannot detect a second photon. The maximum flux rate provided by the invention appears to be at least about 10 million counts per second, in contrast to about 100 thousand counts per second for time-domain techniques. This 100-fold improvement may reflect a decreased PPR and a decreased sensitivity to lost photons. The PPR is reduced to less than about 10 nanoseconds, in contrast to greater than about 100 nanoseconds for the best time-domain apparatus. In addition, the CLIP technique is less sensitive to lost photons because they do not appear to change the measured distribution. FIG. 13 shows a possible explanation for this increased sensitivity. In the time domain (Panel A), photons lost in the dead time will always have a greater delay than the measured photon. The lost photons therefore skew the lifetime measurement to shorter values. To avoid this error, the maximum (average) flux rate should be less than one one-hundredth of the peak flux rate (the inverse of the PPR), or about 100 thousand counts per second. In contrast, in the frequency-domain technique provided by the invention (Panel B), photons with long delays that are preferentially lost can correspond to a phase delay shorter or longer than the first photon. For example, a lost long-delay photon could have arrived in the next period with a lesser phase delay.

The CLIP apparatus and method may be distinguished from synchronous photon counting (or the digital lock-in technique), which is typified by the Stanford Research Systems SR400 dual channel gated photon counter. Synchronous photon counting is used to subtract dark counts automatically from a photon-counted signal. In particular, the luminescent system is excited with a pulse of light at a low repetition rate (typically from an optical chopper). The photon counter sums all counts that arrive while the system is illuminated and subtracts all counts while it is not. If the duration of summation is equal to the duration of subtraction, the dark counts of the photodetector will be properly subtracted from the emission signal. The output is the dark-subtracted intensity of the luminescent system. The synchronous photon counting technique is not used to measure luminescence lifetime, even for extremely long lifetimes. Apparatus for synchronous photon counting systems could be converted in a limited way to CLIP only by adding key CLIP components.

Although the invention has been disclosed in its preferred forms, the specific embodiments thereof as disclosed and illustrated herein are not to be considered in a limiting sense, because numerous variations are possible. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

What is claimed is:

1. A method for measuring a temporal property of a luminescent sample, the method comprising:
   illuminating the sample with intensity-modulated incident light, where the modulation is characterized by a characteristic time;
   detecting luminescence emitted from the sample in response to the illumination with incident light;
   counting the number of photons in the detected luminescence during a preselected portion of the characteristic time;
   computing a frequency-domain quantity based on the number of counted photons; and
   determining the temporal property based on the frequency-domain quantity.

2. The method of claim 1, where the temporal property is a luminescence lifetime or a reorientational correlation time.

3. The method of claim 1, where the intensity of the incident light is modulated periodically with time, and where the characteristic time is the period of the modulation.

4. The method of claim 3, where the incident light is modulated sinusoidally.

5. The method of claim 3, where the period is less than about 10 milliseconds.

6. The method of claim 1, where the detected luminescence is detected substantially exclusively from a sensed volume of the sample.

7. The method of claim 1, where the detected luminescence is detected throughout the characteristic time.

8. The method of claim 1, where the steps of illuminating and detecting are performed simultaneously.

9. The method of claim 1, where the preselected portion is at least one-eighth of the characteristic time.

10. The method of claim 1, the preselected portion being a first preselected portion, further comprising:
    counting the number of photons in the detected luminescence during a second preselected portion of the characteristic time, where the first and second portions correspond to at least partially different portions of the characteristic time.

11. The method of claim 10, where the first and second portions overlap.

12. The method of claim 10, where the first and second portions do not overlap.

13. The method of claim 1, further comprising:
    counting the number of photons in the detected luminescence during additional preselected portions of the characteristic time, where the total number of portions is an integer power of two.

14. The method of claim 1, where the step of counting the number of photons includes the steps of converting the detected luminescence to a signal, and discriminating photons from noise based on their relative contributions to the signal.

15. The method of claim 1, where the frequency-domain quantity is a phase shift and/or a demodulation of the detected luminescence relative to the incident light.

16. The method of claim 1, where the step of determining the temporal property includes the step of correcting for intensity variations in the light source.

17. The method of claim 1, where the step of determining the temporal property includes the step of correcting for instrumental factors.

18. The method of claim 1, further comprising:
    repeating the steps of illuminating, detecting, and counting with the same sample before determining the temporal property, where the number of counted photons used to compute the frequency-domain quantity is the sum of the number of photons counted in each repetition of illuminating and detecting.

19. The method of claim 1, further comprising:
    automatically repeating the steps of illuminating, detecting, counting, and determining the temporal property with a series of samples.

20. An apparatus for measuring a temporal property of a luminescent sample, the apparatus comprising:

a light source for producing intensity-modulated excitation light;

an excitation optical relay structure that directs the intensity-modulated excitation light toward the sample, so that the sample may be induced to emit intensity-modulated emission light;

a detector for detecting light;

an emission optical relay structure that directs light from the sample toward the detector, so that intensity-modulated emission light from the sample may be detected; and a discrete analyzer operatively connected to the detector, where the analyzer includes a counter that determines the number of photons in the detected emission light, and where the analyzer determines the temporal property based on a frequency-domain quantity computed from the number of photons.

21. The apparatus of claim 20, where the temporal property is a luminescence lifetime or a reorientational correlation time.

22. The apparatus of claim 20, where the excitation light is modulated sinusoidally.

23. The apparatus of claim 20, where the frequency-domain quantity is a phase shift and/or a demodulation of the detected luminescence relative to the incident light.

24. The apparatus of claim 20, where the discrete analyzer is configured to correct for at least one of the following: intensity variations in the light source, and instrumental factors.

25. The apparatus of claim 20, where the emission optical relay structure is capable of transmitting light substantially exclusively from a sensed volume of the sample.

26. A method for measuring a temporal property of a luminescent sample, the method comprising:

illuminating the sample with intensity-modulated incident light capable of exciting luminescence in the sample, where the modulation of the intensity-modulated light is characterized by a characteristic time;

measuring luminescence emitted from the sample during first and second preselected portions of the characteristic time, where the first and second portions overlap; and determining the temporal property based on the measured luminescence during the first and second portions.

27. The method of claim 26, where the temporal property is a luminescence lifetime or a reorientational correlation time.

28. The method of claim 26, where the step of measuring luminescence includes the step of counting the number of photons in the detected luminescence.

29. The method of claim 26, where the step of measuring luminescence includes the step of performing an analog integration of a signal proportional to the number of photons in the detected luminescence.

30. The method of claim 26, where the step of determining the temporal property includes the step of computing a frequency-domain quantity.

31. The method of claim 30, where the frequency-domain quantity is a phase shift and/or a demodulation of the detected luminescence relative to the incident light.

32. The method of claim 26, further comprising:

measuring luminescence emitted from the sample during additional preselected portions of the characteristic time, where the total number of portions is an integer power of two.

33. An apparatus for measuring a temporal property of a luminescent sample, the apparatus comprising:

a light source for producing intensity-modulated excitation light;

an excitation optical relay structure that directs the intensity-modulated excitation light toward the sample, so that the sample may be induced to emit intensity-modulated emission light;

a detector for detecting light;

an emission optical relay structure that directs light from the sample toward the detector, so that intensity-modulated emission light from the sample may be detected; and a discrete analyzer operatively connected to the detector, where the analyzer is configured to measure light emitted from the sample during overlapping intervals and to determine the temporal property based on the measured light.

34. The apparatus of claim 33, where the temporal property is a luminescence lifetime or a reorientational correlation time.

35. The apparatus of claim 33, where the discrete analyzer is configured to determine the temporal property based on a frequency-domain quantity computed using the measured light.

36. The apparatus of claim 33, where the frequency-domain quantity is a phase shift and/or a demodulation of the detected luminescence relative to the incident light.

* * * * *